United States Patent
Duncan

(10) Patent No.: US 11,548,913 B2
(45) Date of Patent: Jan. 10, 2023

(54) THERAPEUTIC COMPOSITIONS INCLUDING PEPTIDES AND USES THEREOF

(71) Applicant: Stealth BioTherapeutics Inc., Needham, MA (US)

(72) Inventor: Scott Duncan, Bedford, MA (US)

(73) Assignee: STEALTH BIOTHERAPEUTICS INC., Needham, MA (US)

(*) Notice: Subject to any disclaimer, the term of this patent is extended or adjusted under 35 U.S.C. 154(b) by 232 days.

(21) Appl. No.: 16/067,514

(22) PCT Filed: Dec. 29, 2016

(86) PCT No.: PCT/US2016/069185
§ 371 (c)(1),
(2) Date: Jun. 29, 2018

(87) PCT Pub. No.: WO2017/117381
PCT Pub. Date: Jul. 6, 2017

(65) Prior Publication Data
US 2021/0206803 A1    Jul. 8, 2021

Related U.S. Application Data

(60) Provisional application No. 62/273,862, filed on Dec. 31, 2015.

(51) Int. Cl.
*C07K 7/06* (2006.01)
*A61P 9/10* (2006.01)
*A61K 38/00* (2006.01)

(52) U.S. Cl.
CPC .............. *C07K 7/06* (2013.01); *A61P 9/10* (2018.01); *A61K 38/00* (2013.01)

(58) Field of Classification Search
CPC .......... A61K 38/00; A61P 9/10; C07K 5/1019; C07K 7/06
See application file for complete search history.

(56) References Cited

U.S. PATENT DOCUMENTS

| | | | |
|---|---|---|---|
| 10,808,008 B2 * | 10/2020 | Szeto | A61P 13/02 |
| 2013/0150283 A1 | 6/2013 | Nudler et al. | |
| 2014/0341879 A1 * | 11/2014 | Borow | A61P 7/02 424/94.64 |

FOREIGN PATENT DOCUMENTS

| | | | | |
|---|---|---|---|---|
| WO | WO-2010/120431 A2 | 10/2010 | | |
| WO | WO-2011/091357 A1 | 7/2011 | | |
| WO | WO-2013/049697 | 4/2013 | | |
| WO | WO2013/086020 | * 6/2013 | ............ | A61K 38/07 |
| WO | WO2013/126775 | * 8/2013 | ............ | A61K 38/07 |
| WO | WO-2014/210056 A1 | 12/2014 | | |

OTHER PUBLICATIONS

Extended Search Report in EP Patent Application No. 16882655.0 dated Jul. 16, 2019 (9 pages).
International Preliminary Report on Patentability on PCT Patent Application No. PCT/US2016/069185 dated Jul. 3, 2018.
International Search Report & Written Opinion on PCT Patent Application No. PCT/US2016/069185 dated Mar. 13, 2017 (5 pages).
Konopinska et al. "Role of guanidine group at the N-terminal porctolin chain in cardioexcitatory effects in insects," International Journal of Peptide and Protein Research, vol. 35 (1990) (pp. 12-16).

* cited by examiner

*Primary Examiner* — Marcela M Cordero Garcia
(74) *Attorney, Agent, or Firm* — Foley & Lardner LLP

(57) ABSTRACT

Disclosed herein are methods and compositions for the treatment and/or prevention of ischemia and ischemia-reperfusion injury comprising administration of at least one peptide disclosed herein, or a pharmaceutically acceptable salt thereof.

6 Claims, 30 Drawing Sheets

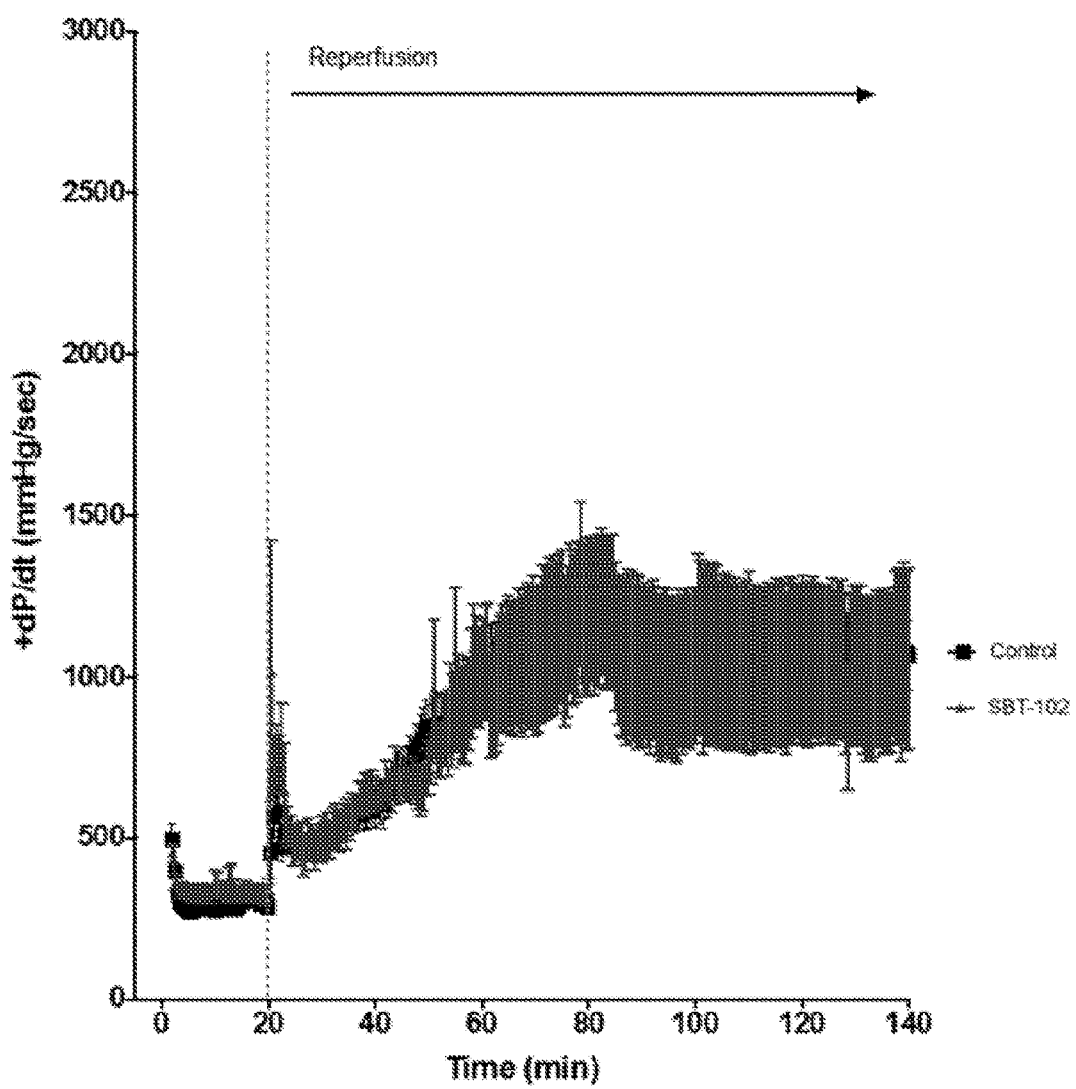

THERAPEUTIC COMPOSITIONS INCLUDING PEPTIDES AND USES THEREOF

CROSS REFERENCE TO RELATED APPLICATION

This application is a U.S. 371c National Stage Application of International Application No. PCT/US2016/069185, filed Dec. 29, 2016, which claims priority to U.S. Provisional Patent Application No. 62/273,862, filed Dec. 31, 2015, the entire contents of which are incorporated herein by reference in their entireties.

TECHNICAL FIELD

Disclosed herein are methods and compositions related to the treatment and/or amelioration of diseases and conditions comprising administration of peptides and/or naturally or artificially occurring derivatives, or a pharmaceutically acceptable salt thereof.

BACKGROUND

The following description is provided to assist the understanding of the reader. None of the information provided or references cited is admitted to be prior art.

Biological cells are generally highly selective as to the molecules that are allowed to pass through the cell membrane. As such, the delivery of compounds, such as small molecules and biological molecules into a cell is usually limited by the physical properties of the compound. The small molecules and biological molecules may, for example, be pharmaceutically active compounds.

SUMMARY

The present technology provides compositions and methods useful in the prevention, treatment and/or amelioration of ischemia-reperfusion injury and/or myocardial infarction.

In one aspect, the present disclosure provides peptides, derivatives, or pharmaceutically acceptable salts thereof. In some embodiments, the peptide is selected from D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$ (SBT-131), D-(Amidine)Arg(propylamine)-L-DMT-L-Lys-L-Phe-NH$_2$(SBT-140), or D-Arg(butylamidine analog)-L-DMT-L-Lys-L-Phe-NH$_2$(SBT-149), wherein DMT is 2',6'-dimethyltyrosine.

In one aspect, the present disclosure provides a composition comprising peptides, derivatives, or pharmaceutically acceptable salts thereof. In some embodiments, the peptide is selected from D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$ (SBT-131), D-(Amidine)Arg(propylamine)-L-DMT-L-Lys-L-Phe-NH$_2$(SBT-140), or D-Arg(butylamidine analog)-L-DMT-L-Lys-L-Phe-NH$_2$(SBT-149), wherein DMT is 2',6'-dimethyltyrosine.

In some embodiments, the composition comprises a peptide, derivative, or a pharmaceutically acceptable salt thereof.

In some embodiments, an amino acid residue in any one of the above peptides may be substituted with a non-natural amino acid residue or a derivative of a naturally occurring amino acid.

In one aspect, the present disclosure provides a method for treating or preventing ischemia-reperfusion injury in a subject by administering to the subject a therapeutically effective amount of a composition comprising an peptide provided herein, or derivatives, or pharmaceutically acceptable salts thereof. In some embodiments, the peptide is selected from D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$ (SBT-131), D-(Amidine)Arg(propylamine)-L-DMT-L-Lys-L-Phe-NH$_2$(SBT-140), or D-Arg(butylamidine analog)-L-DMT-L-Lys-L-Phe-NH$_2$(SBT-149). In some embodiments, the ischemia-reperfusion injury is cardiac ischemia-reperfusion injury. In some embodiments, the peptide is administered orally, topically, systemically, intravenously, subcutaneously, intraperitoneally, or intramuscularly.

In one aspect, the present technology provides a method for treating a myocardial infarction in a subject to prevent injury to the heart upon reperfusion by administering to the subject a therapeutically effective amount of a composition comprising an peptide provided herein, or derivatives, or pharmaceutically acceptable salts thereof to prevent the initiation or progression of the infarction. In some embodiments, the peptide is selected from D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$(SBT-131), D-(Amidine)Arg(propylamine)-L-DMT-L-Lys-L-Phe-NH$_2$(SBT-140), or D-Arg(butylamidine analog)-L-DMT-L-Lys-L-Phe-NH$_2$ (SBT-149). In some embodiments, the peptide is administered orally, topically, systemically, intravenously, subcutaneously, intraperitoneally, or intramuscularly.

BRIEF DESCRIPTION OF THE DRAWINGS

FIGS. 5A-D are graphs showing an illustrative example of a tetrapeptide of that does not attenuate cardiac ischemia-reperfusion injury in a modified Langendorff rat heart model. Excised Sprague-Dawley rat hearts were reperfused as described in Example 1. Data is shown for infarct size expressed as a percentage of AAR (FIG. 5A), left ventricular developed pressure (LVDP) (FIG. 5B), and maximal rates of contraction and relaxation (±dP/dt) (FIGS. 5C-D) for control hearts and hearts treated with D-Arg-L-Dmt-L-Orn-L-Phe-$NH_2$ (SBT-102).

DETAILED DESCRIPTION

Figure 1A:
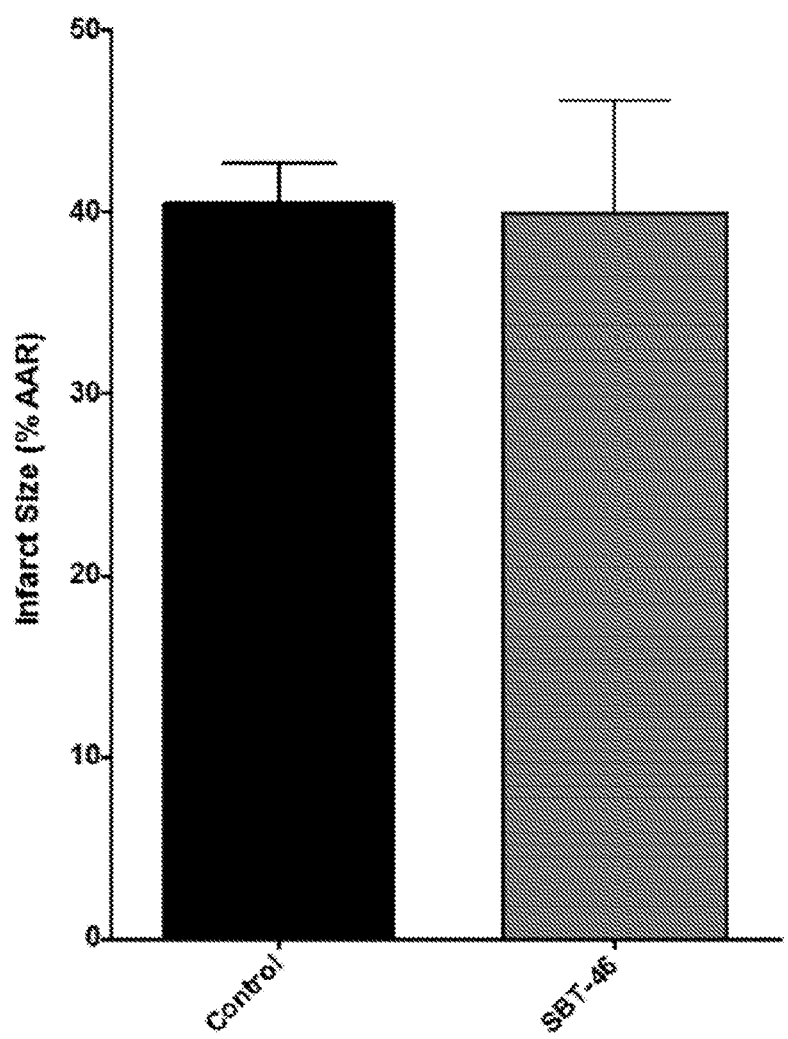
FIGS. 1A-D are graphs showing an illustrative example of a tetrapeptide that does not attenuate cardiac ischemia-reperfusion injury in a modified Langendorff rat heart model. Excised Sprague-Dawley rat hearts were reperfused as described in Example 1. Data is shown for infarct size expressed as a percentage of area at risk (AAR) (FIG. 1A), left ventricular developed pressure (LVDP) (FIG. 1B), and maximal rates of contraction and relaxation (±dP/dt) (FIGS. 1C-D) for control hearts and hearts treated with D-Arg-D-Dmt-D-Lys-L-Phe-NH$_2$ (SBT-46).

It is to be appreciated that certain aspects, modes, embodiments, variations and features of the present technology are described below in various levels of detail in order to provide a substantial understanding of the present technology.

The present disclosure provides compositions comprising a peptide of the present disclosure. Also provided are therapeutic methods comprising administration of the compositions useful in the prevention, treatment and/or amelioration of diseases and conditions.

I. Select Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, the term "about" encompasses the range of experimental error that may occur in a measurement and will be clear to the skilled artisan.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogues and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogues refer to compounds that have the same basic chemical structure as a naturally-occurring amino acid, i.e., an α-carbon that is bound to a carboxyl group, an amino group, and an R group, e.g., homoserine, norleucine, methionine sulfoxide, methionine methyl sulfonium. Such analogues have modified R groups (e.g., norleucine) or modified peptide backbones, but retain the same basic chemical structure as a naturally-occurring amino acid. Amino acid mimetics refer to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, "chemically bonded" refers to an attachment by means of a covalent bond. "Physically bonded" refers to an attachment by means of a physical interaction (non-covalent bond). Examples are but not limited to H-bonds, pi stacking electrostatic interactions, matrices, salts, co-crystals, occlusion, solvates, hydrates, Van der Waal forces and London dispersion forces.

As used herein, the term "effective amount" refers to a quantity sufficient to achieve a desired therapeutic and/or prophylactic effect, e.g., an amount which results in the prevention of, or a decrease in a disease or disorder or one or more signs or symptoms associated with a disease or disorder. In the context of therapeutic or prophylactic applications, the amount of a composition administered to the subject will depend on the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

As used herein, an "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated peptide would be free of materials that would interfere with diagnostic or therapeutic uses of the agent. Such interfering materials may include enzymes, hormones and other proteinaceous and nonproteinaceous solutes.

As used herein, the term "non-naturally-occurring" refers to a composition which is not found in this form in nature. A non-naturally-occurring composition can be derived from a naturally-occurring composition, e.g., as non-limiting examples, via purification, isolation, concentration, chemical modification (e.g., addition or removal of a chemical group), and/or, in the case of mixtures, addition or removal of ingredients or compounds. Alternatively, a non-naturally-occurring composition can comprise or be derived from a non-naturally-occurring combination of naturally-occurring compositions. Thus, a non-naturally-occurring composition can comprise a mixture of purified, isolated, modified and/or concentrated naturally-occurring compositions, and/or can comprise a mixture of naturally-occurring compositions in forms, concentrations, ratios and/or levels of purity not found in nature.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, "prevention" or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, the term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York), incorporated herein by reference in its entirety for any and all purposes. Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenyl-methyloxycarbonyl (Fmoc), acetyl (Ac), trifluoroacetyl, tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyldimethoxybenzyloxycarbonyl (DDZ), 5-bromo-7-nitroindolinyl, and the like, as well as phosphoryl protecting groups as exemplified by the following structure:

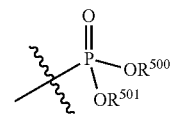

where $R^{500}$ and $R^{501}$ are each independently hydrogen or a substituted or unsubstituted alkyl, aryl, heterocyclyl, heteroaryl group. Hydroxyl protecting groups include, but are not limited to, Fmoc, TBS, photolabile protecting groups (such as nitroveratryl oxymethyl ether (Nvom)), Mom (methoxy methyl ether), and Mem (methoxyethoxy methyl ether), NPEOC (4-nitrophenethyloxycarbonyl) and NPEOM (4-nitrophenethyloxymethyloxycarbonyl).

As used herein, the terms "subject," "individual," or "patient" can be an individual organism, a vertebrate, a mammal, or a human.

As used herein, a "therapeutically effective amount" of a compound refers to compound levels in which the physiological effects of a disease or disorder are, at a minimum, ameliorated. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

II. Peptides of the Present Technology

Described herein are peptides for therapeutic use. The peptides of the present technology include four amino acids that are covalently joined by peptide bonds.

In some embodiments, the peptide of the present technology is selected from the following peptides:

1) D-Arg-L-DMT-L-Ala-L-Phe-NH₂

(SBT-68)

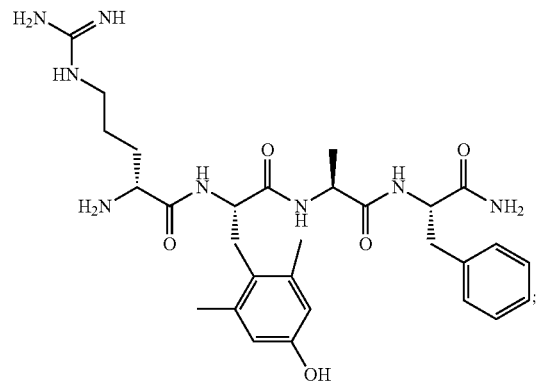

2) (Ac)-D-Arg-L-DMT-L-Lys-L-Phe-NH₂

(SBT-85)

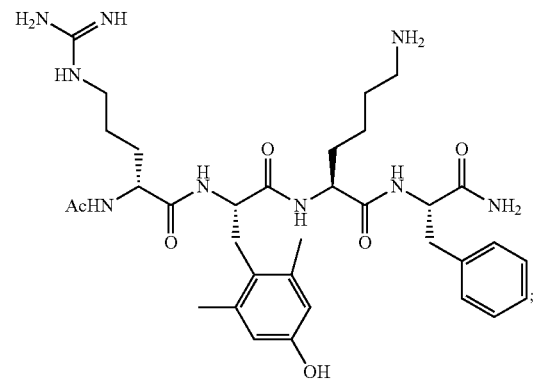

3) D-Arg-L-Dmt-L-His-L-Phe-NH₂

(SBT-100)

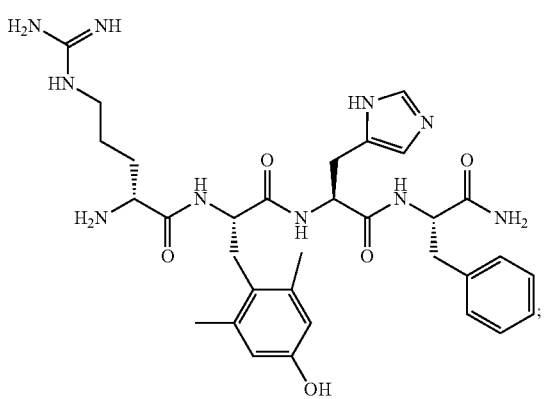

4) D-Orn-L-DMT-L-Lys-L-Phe-NH₂

(SBT-131)

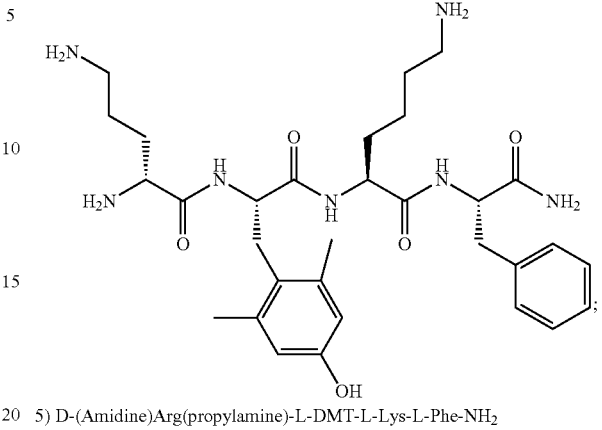

5) D-(Amidine)Arg(propylamine)-L-DMT-L-Lys-L-Phe-NH₂

(SBT-140)

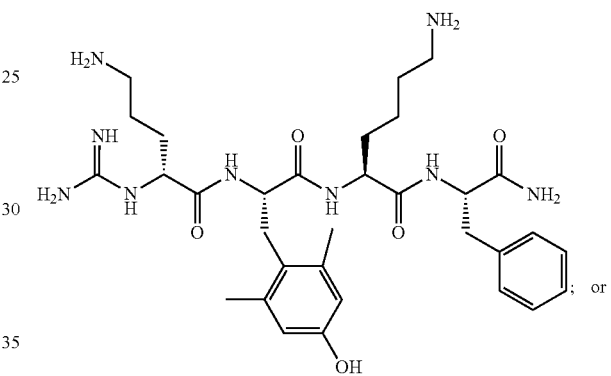

6) D-Arg(butylamidine analog)-L-DMT-L-Lys-L-Phe-NH₂

(SBT-149)

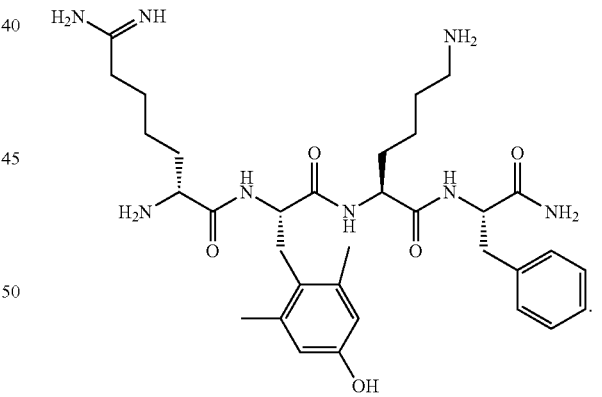

The peptides useful in the present technology can contain one or more non-naturally occurring amino acids. The non-naturally occurring amino acids may be (L-), dextrorotatory (D), or mixtures thereof. In some embodiments, the peptide has no amino acids that are naturally occurring.

In some embodiments, an amino acid residue in any one of the peptides disclosed herein may be substituted with a non-natural amino acid residue or a derivative of a naturally occurring amino acid.

Non-naturally occurring amino acids are those amino acids that typically are not synthesized in normal metabolic processes in living organisms, and do not naturally occur in proteins. In certain embodiments, the non-naturally occurring amino acids useful in the present technology are also not recognized by common proteases.

The non-naturally occurring amino acid can be present at any position in the peptide. For example, the non-naturally occurring amino acid can be at the N terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenyl acetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the present methods is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol.

Another such modification includes derivatization of an amino group of a lysine, arginine, or histidine residue. For example, such amino groups can be alkylated or acylated. Some suitable acyl groups include, for example, a benzoyl group or an alkanoyl group comprising any of the $C_1$-$C_4$ alkyl groups mentioned above, such as an acetyl or propionyl group.

In some embodiments, the non-naturally occurring amino acids are resistant, and in some embodiments insensitive, to common proteases. Examples of non-naturally occurring amino acids that are resistant or insensitive to proteases include the dextrorotatory (D-) form of any of the above-mentioned naturally occurring L-amino acids, as well as L- and/or D non-naturally occurring amino acids. The D-amino acids do not normally occur in proteins, although they are found in certain peptide antibiotics that are synthesized by means other than the normal ribosomal protein synthetic machinery of the cell, as used herein, the D-amino acids are considered to be non-naturally occurring amino acids.

In order to minimize protease sensitivity, the peptides useful in the methods of the present technology should have less than five, less than four, less than three, or less than two contiguous L-amino acids recognized by common proteases, irrespective of whether the amino acids are naturally or non-naturally occurring. In some embodiments, the peptide has only D-amino acids, and no L-amino acids.

If the peptide contains protease sensitive sequences of amino acids, at least one of the amino acids is a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine. In some embodiments, at least one of the amides in the peptide backbone are alkylated, thereby conferring protease resistance.

In some embodiments, carboxyl groups, especially the terminal carboxyl group of a C-terminal amino acid, are amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethyl amido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the peptides of the present technology may also be amidated wherever they occur within the peptide. The amidation at these internal positions may be with ammonia or any of the primary or secondary amines described herein.

In one embodiment, the peptide useful in the methods of the present technology is a tripeptide having two net positive charges and at least one aromatic amino acid. In a particular embodiment, the peptide useful in the methods of the present technology is a tripeptide having two net positive charges and two aromatic amino acids.

In some embodiments, the peptide has an arginine residue or an arginine derivative at the N-terminus (i.e., the first amino acid position). Suitable derivatives of arginine include, for example, D-arginine. Examples of peptides that have an arginine residue or an arginine derivative at the N-terminus include a peptide having the formula D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$ (SBT-100), D-Orn-L-DMT-L-Lys-L-Phe-NH$_2$(SBT-131), D-(Amidine)Arg(propylamine)-L-DMT-L-Lys-L-Phe-NH$_2$ (SBT-140), or D-Arg(butylamidine analog)-L-DMT-L-Lys-L-Phe-NH$_2$(SBT-149).

In some embodiments, the peptide has a tyrosine residue or a tyrosine derivative at the second amino acid position. Suitable derivatives of tyrosine include 2'-methyltyrosine (Mmt); 2',6'-dimethyltyrosine (DMT); 3',5'-dimethyltyrosine (3'5'Dmt); N,2',6'-trimethyltyrosine (Tmt); and 2'-hydroxy-6'-methyltyrosine (Hmt). Examples of peptides that have a tyrosine residue or a tyrosine derivative at the second amino acid position include a peptide having the formula D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$ (SBT-131), D-(Amidine)Arg(propylamine)-L-DMT-L-Lys-L-Phe-NH$_2$ (SBT-140), or D-Arg(butylamidine analog)-L-DMT-L-Lys-L-Phe-NH$_2$(SBT-149).

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W).

Substitutions of an amino acid in a peptide by another amino acid in the same group are referred to as a conservative substitution and may preserve the physicochemical characteristics of the original peptide. In contrast, substitutions of an amino acid in a peptide by another amino acid in a different group are generally more likely to alter the characteristics of the original peptide.

Any amino acids in the peptides disclosed herein may be in either the L- or the D-configuration.

III. Uses of Compositions of the Present Technology

The following discussion is presented by way of example only, and is not intended to be limiting.

Ischemia is reduction or decrease in blood supply to a tissue or an organ and has many different causes. Ischemia may be local, e.g., caused by thrombus or embolus, or more global, e.g., due to low perfusion pressure. An ischemic event can lead to hypoxia (reduced oxygen) and/or anoxia (absence of oxygen).

Ischemia in a tissue or organ of a mammal is a multifaceted pathological condition that is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle.

The organ affected by ischemia or hypoxia may be any organ that is subject to ischemia or hypoxia. By way of example, but not by way of limitation, cardiac muscle ischemia or hypoxia is commonly caused by atherosclerotic or thrombotic blockages, which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Reperfusion is the restoration of blood flow to any organ or tissue in which the flow of blood is decreased or blocked. For example, blood flow can be restored to any organ or tissue affected by ischemia. The restoration of blood flow (reperfusion) can occur by any method known to those in the art. For instance, reperfusion of ischemic cardiac tissues may arise from angioplasty, coronary artery bypass graft, or the use of thrombolytic drugs.

Ischemia-reperfusion injury is the cellular or tissue damage caused when blood supply returns to the affected area after a period of ischemia. The lack of oxygen and nutrients during ischemia creates a condition in which the restoration of circulation results damage to the tissues. By way of example, but not by way of limitation, forms of myocardial reperfusion injury including reperfusion-induced arrhythmias, myocardial stunning, microvascular obstruction manifesting in sluggish coronary blood flow, and lethal myocardial reperfusion injury (i.e., reperfusion-induced death of cardiomyocytes that were viable at the end of the index ischemic event). Studies have suggested that lethal myocardial reperfusion injury accounts for about 50% of the final myocardial infarct size.

Therapeutic Methods

One aspect of the present technology includes methods of treating ischemic injury and/or side effects associated with existing therapeutics against ischemic injury in a subject diagnosed as having, suspected as having, or at risk of having ischemic injury. In therapeutic applications, compositions or medicaments comprising at least one peptide disclosed herein (e.g., D-Arg-L-DMT-L-Ala-L-Phe-$NH_2$ (SBT-68), (Ac)-D-Arg-L-DMT-L-Lys-L-Phe-$NH_2$ (SBT-85), D-Arg-L-Dmt-L-His-L-Phe-$NH_2$(SBT-100), D-Orn-L-DMT-L-Lys-L-Phe-$NH_2$ (SBT-131), D-(Amidine)Arg(propylamine)-L-DMT-L-Lys-L-Phe-$NH_2$(SBT-140), or D-Arg (butylamidine analog)-L-DMT-L-Lys-L-Phe-$NH_2$(SBT-149)), or a pharmaceutically acceptable salt thereof, such as acetate, tartrate, or trifluoroacetate salt, is administered to a subject suspected of, or already suffering from ischemic injury in an amount sufficient to cure, or at least partially arrest, the symptoms of the disease, including its complications and intermediate pathological phenotypes in development of the disease. Subjects suffering from ischemic injury can be identified by any or a combination of diagnostic or prognostic assays known in the art. By way of example, but by way of limitation, in some embodiments, the ischemic injury is related to cardiac ischemia, brain ischemia, renal ischemia, cerebral ischemia, intestinal ischemia, hepatic ischemia, or myocardial infarction.

By way of example, but not by way of limitation, typical symptoms of cardiac ischemia include, but are not limited to, angina (e.g., chest pain and pressure), shortness of breath, palpitations, weakness, dizziness, nausea, sweating, rapid heartbeat, and fatigue.

In some embodiments, treatment of subjects diagnosed with cardiac ischemia with at least one peptide disclosed herein ameliorates or eliminates of one or more of the following symptoms of cardiac ischemia: angina (e.g., chest pain and pressure), shortness of breath, palpitations, weakness, dizziness, nausea, sweating, rapid heartbeat, and fatigue.

By way of example, but not by way of limitation, typical symptoms of renal ischemia include, but are not limited to, uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment of subjects diagnosed with renal ischemia with at least one peptide disclosed herein ameliorates or eliminates of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

By way of example, but not by way of limitation, typical symptoms of cerebral (or brain) ischemia include, but are not limited to, blindness in one eye, weakness in one arm or leg, weakness in one entire side of the body, dizziness, vertigo, double vision, weakness on both sides of the body, difficulty speaking, slurred speech, and the loss of coordination.

In some embodiments, treatment of subjects diagnosed with cerebral (or brain) ischemia with at least one peptide disclosed herein ameliorates or eliminates of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

In another aspect, the present technology includes methods of treating ischemia-reperfusion injury and/or side effects associated with existing therapeutics against ischemia-reperfusion injury. In therapeutic applications, compositions or medicaments comprising at least one peptide disclosed herein (e.g., D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$(SBT-131), D-(Amidine)Arg(propylamine)-L-DMT-L-Lys-L-Phe-NH$_2$(SBT-140), or D-Arg (butylamidine analog)-L-DMT-L-Lys-L-Phe-NH$_2$ (SBT-149)), or a pharmaceutically acceptable salt thereof, such as acetate, tartrate or trifluoroacetate, is administered to a subject suspected of, or already suffering from ischemic-reperfusion injury in an amount sufficient to cure, or at least partially arrest, the symptoms of the disease, including its complications and intermediate pathological phenotypes in development of the disease. Subjects suffering from ischemic-reperfusion injury can be identified by any or a combination of diagnostic or prognostic assays known in the art. By way of example, but by way of limitation, in some embodiments, the ischemia-reperfusion injury is related to cardiac ischemia, brain ischemia, renal ischemia, cerebral ischemia, intestinal ischemia, and hepatic ischemia. In some embodiments, the peptides disclosed herein are useful in the treatment of cardiac ischemia-reperfusion injury.

In some embodiments, the peptides disclosed herein are useful in treating myocardial infarction in a subject to prevent injury to the heart upon reperfusion. In some embodiments, the present technology relates to a method of coronary revascularization, comprising administering to a mammalian subject a therapeutically effective amount of one or more peptides selected from: D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$(SBT-131), D-(Amidine) Arg(propylamine)-L-DMT-L-Lys-L-Phe-NH$_2$ (SBT-140) or D-Arg(butylamidine analog)-L-DMT-L-Lys-L-Phe-NH$_2$ (SBT-149), or a pharmaceutically acceptable salt thereof, of the present technology and performing a coronary artery bypass graft (CABG) procedure on the subject.

In some embodiments, treatment of myocardial infarction with the peptides disclosed herein reduces infarct size, increases LVDP, and increases maximal rates of contraction and relaxation (±dP/dt).

Prophylactic Methods

In some embodiments, the present technology provides methods for preventing or delaying the onset of ischemic injury or symptoms of ischemic injury in a subject at risk of having ischemia injury. In some embodiments, the present technology provides methods for preventing or reducing the symptoms of ischemic injury in a subject at risk of having ischemia injury.

In some embodiments, the present technology provides methods for preventing or delaying the onset of ischemia-reperfusion injury or symptoms of ischemia-reperfusion injury in a subject at risk of having ischemia-reperfusion injury. In some embodiments, the present technology provides methods for preventing or reducing the symptoms of ischemia-reperfusion injury in a subject at risk of having ischemia-reperfusion injury.

In some embodiments, the ischemic injury, the ischemia-reperfusion injury, or symptoms of ischemic or ischemia-reperfusion injury is related to cardiac ischemia, brain ischemia, renal ischemia, cerebral ischemia, intestinal ischemia, and hepatic ischemia. In some embodiments, the ischemic injury is myocardial infarction.

In some embodiments, the peptides disclosed herein are useful in the treatment or prevention of cardiac ischemia-reperfusion injury. In some embodiments, the peptides disclosed herein are useful in the prevention of cardiac ischemia-reperfusion injury.

Subjects at risk for ischemic injury or ischemia-reperfusion injury can be identified by, e.g., any or a combination of diagnostic or prognostic assays known in the art. In prophylactic applications, pharmaceutical compositions or medicaments of peptides (e.g., D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$ (SBT-100), D-Orn-L-DMT-L-Lys-L-Phe-NH$_2$(SBT-131), D-(Amidine) Arg(propylamine)-L-DMT-L-Lys-L-Phe-NH$_2$(SBT-140), or D-Arg(butylamidine analog)-L-DMT-L-Lys-L-Phe-NH$_2$ (SBT-149)), or a pharmaceutically acceptable salt thereof, such as acetate, tartrate, or trifluoroacetate salt, are administered to a subject susceptible to, or otherwise at risk of for ischemic injury or ischemia-reperfusion injury in an amount sufficient to eliminate, reduce the risk, or delay the onset of the disease, including biochemical, histologic and/or behavioral symptoms of the disease, its complications and intermediate pathological phenotypes presenting during development of the disease or reduce the symptoms and/or complications and intermediate pathological phenotypes presenting during development of the disease. Administration of a prophylactic peptide can occur prior to the manifestation of symptoms characteristic of the disease or disorder, such that the disease or disorder is prevented, delayed in its progression, or the severity of the symptoms or side effects of the disease or disorder are reduced.

By way of example, but not by way of limitation, in some embodiments, subjects may be at risk for cardiac ischemia if they have coronary artery disease (atherosclerosis), blood clots, and coronary artery spasm.

By way of example, but not by way of limitation, in some embodiments, subjects may be at risk for renal ischemia if they have kidney injury (e.g., acute kidney injury) and/or injuries or complications from surgeries in which the kidneys are deprived of normal blood flow for extended periods of time (e.g., heart-bypass surgery).

By way of example, but not by way of limitation, in some embodiments, subjects may be at risk for cerebral ischemia if they have sickle cell anemia, compressed blood vessels, ventricular tachycardia, plaque buildup in the arteries, blood clots, extremely low blood pressure as a result of heart attack, had a stroke, or congenital heart defects.

For therapeutic and/or prophylactic applications, a composition comprising at least one peptide disclosed herein (e.g., D-Arg-L-DMT-L-Ala-L-Phe-$NH_2$ (SBT-68), (Ac)-D-Arg-L-DMT-L-Lys-L-Phe-$NH_2$ (SBT-85), D-Arg-L-Dmt-L-His-L-Phe-$NH_2$(SBT-100), D-Orn-L-DMT-L-Lys-L-Phe-$NH_2$(SBT-131), D-(Amidine)Arg(propylamine)-L-DMT-L-Lys-L-Phe-$NH_2$ (SBT-140), or D-Arg(butylamidine analog)-L-DMT-L-Lys-L-Phe-$NH_2$ (SBT-149)), or a pharmaceutically acceptable salt thereof, such as acetate, tartrate, or trifluoroacetate salt, is administered to a subject in need thereof. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year.

In some embodiments, treatment with at least one peptide disclosed herein will prevent or delay the onset of one or more of the following symptoms of cardiac ischemia: angina (e.g., chest pain and pressure), shortness of breath, palpitations, weakness, dizziness, nausea, sweating, rapid heartbeat, and fatigue.

In some embodiments, treatment with at least one peptide disclosed herein will prevent or delay the onset of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment with at least one peptide disclosed herein will prevent or delay the onset of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

Determination of the Biological Effect of the Peptides of the Present Technology In various embodiments, suitable in vitro or in vivo assays are performed to determine the effect of a specific composition of the present technology and whether its administration is indicated for treatment. In various embodiments, in vitro assays can be performed with representative animal models, to determine if a given peptide (e.g., D-Arg-L-DMT-L-Ala-L-Phe-$NH_2$ (SBT-68), (Ac)-D-Arg-L-DMT-L-Lys-L-Phe-$NH_2$ (SBT-85), D-Arg-L-Dmt-L-His-L-Phe-$NH_2$ (SBT-100), D-Orn-L-DMT-L-Lys-L-Phe-$NH_2$(SBT-131), D-(Amidine)Arg(propylamine)-L-DMT-L-Lys-L-Phe-$NH_2$ (SBT-140), or D-Arg(butylamidine analog)-L-DMT-L-Lys-L-Phe-$NH_2$ (SBT-149)), or a pharmaceutically acceptable salt thereof, of the present technology, exerts the desired effect in treating a disease or condition. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

IV. Synthesis of Compositions of the Present Technology

The compounds useful in the methods of the present disclosure (e.g., peptides, or derivatives, or pharmaceutically acceptable salts thereof) may be synthesized by any method known in the art.

The peptides disclosed herein (e.g., D-Arg-L-DMT-L-Ala-L-Phe-$NH_2$ (SBT-68), (Ac)-D-Arg-L-DMT-L-Lys-L-Phe-$NH_2$ (SBT-85), D-Arg-L-Dmt-L-His-L-Phe-$NH_2$ (SBT-100), D-Orn-L-DMT-L-Lys-L-Phe-$NH_2$(SBT-131), D-(Amidine)Arg(propylamine)-L-DMT-L-Lys-L-Phe-$NH_2$ (SBT-140), or D-Arg(butylamidine analog)-L-DMT-L-Lys-L-Phe-$NH_2$ (SBT-149)), may be synthesized by any method known in the art. Exemplary, non-limiting methods for chemically synthesizing the protein include those described by Stuart and Young in "*Solid Phase Peptide Synthesis*," Second Edition, Pierce Chemical Company (1984), and in "*Solid Phase Peptide Synthesis*," Methods Enzymol. 289, Academic Press, Inc., New York (1997).

Recombinant peptides may be generated using conventional techniques in molecular biology, protein biochemistry, cell biology, and microbiology, such as those described in *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, Meth. Enzymol., (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Peptide precursors may be made by either chemical (e.g., using solution and solid phase chemical peptide synthesis) or recombinant syntheses known in the art. Precursors of e.g., amidated peptides of the present technology may be made in like manner. In some embodiments, recombinant production is believed significantly more cost effective. In some embodiments, precursors are converted to active peptides by amidation reactions that are also known in the art. For example, enzymatic amidation is described in U.S. Pat. No. 4,708,934 and European Patent Publications 0 308 067 and 0 382 403. Recombinant production can be used for both the precursor and the enzyme that catalyzes the conversion of the precursor to the desired active form of the peptide. Such recombinant production is discussed in Biotechnology, Vol. 11 (1993) pp. 64-70, which further describes a conversion of a precursor to an amidated product. During amidation, a keto-acid such as an alpha-keto acid, or salt or ester thereof, wherein the alpha-keto acid has the molecular structure RC(O)C(O)OH, and wherein R is selected from the group consisting of aryl, a $C_1$-$C_4$ hydrocarbon moiety, a halogenated or hydroxylated $C_1$-$C_4$ hydrocarbon moiety, and a $C_1$-$C_4$ carboxylic acid, may be used in place of a catalase co-factor. Examples of these keto acids include, but are not limited to, ethyl pyruvate, pyruvic acid and salts thereof, methyl pyruvate, benzoyl formic acid and salts thereof, 2-ketobutyric acid and salts thereof, 3-methyl-2-oxobutanoic acid and salts thereof, and 2-keto glutaric acid and salts thereof.

In some embodiments, the production of the recombinant peptide may proceed, for example, by producing glycine-extended precursor in *E. coli* as a soluble fusion protein with glutathione-S-transferase. An α-amidating enzyme catalyzes conversion of precursors to active peptide. That enzyme is recombinantly produced, for example, in Chinese Hamster Ovary (CHO) cells as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

V. Modes of Administration

Any method known to those in the art for contacting a cell, organ or tissue with at least one peptide disclosed herein (e.g., D-Arg-L-DMT-L-Ala-L-Phe-$NH_2$ (SBT-68), (Ac)-D-Arg-L-DMT-L-Lys-L-Phe-$NH_2$ (SBT-85), D-Arg-L-Dmt-L-His-L-Phe-$NH_2$(SBT-100), D-Orn-L-DMT-L-Lys-L-Phe-$NH_2$(SBT-131), D-(Amidine)Arg(propylamine)-L-DMT-L-Lys-L-Phe-$NH_2$(SBT-140), or D-Arg(butylamidine analog)-L-DMT-L-Lys-L-Phe-$NH_2$ (SBT-149)), or pharmaceutically acceptable salt thereof, may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of an peptide or pharmaceutically acceptable salt thereof, of the present technology, such as those described herein, to a mammal such as a human. When used in vivo for therapy, at least one peptide or pharmaceutically acceptable salt thereof, of the present technology is administered to a mammal in an amount effective in obtaining the desired result or treating the mammal. The effective amount is determined during pre-clinical trials and clinical trials by methods familiar to physicians and clinicians. The dose and dosage regimen will depend upon the degree of the infection in the subject, the characteristics of the particular peptide or pharmaceutically acceptable salt thereof, of the present technology used, e.g., its therapeutic index, the subject, and the subject's history.

An effective amount of at least one peptide or pharmaceutically acceptable salt thereof, of the present technology useful in the present methods, such as in a pharmaceutical composition or medicament, may be administered to a mammal in need thereof by any of a number of well-known methods for administering pharmaceutical compositions or medicaments. The peptide or pharmaceutically acceptable salt thereof, of the present technology may be administered systemically or locally.

The peptide or pharmaceutically acceptable salt thereof, of the present technology may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regimen). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when an peptide or pharmaceutically acceptable salt thereof, of the present technology contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N' dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic, and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic mono-carboxylic acids (e.g., acetic, butyric, formic, propionic, and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, acetate, tartrate, tosylate, fumarate, trifluoroacetate, and the like.

The peptide or pharmaceutically acceptable salt thereof, of the present technology described herein can be incorporated into pharmaceutical compositions for administration, to a subject for the treatment or prevention of a disorder described herein. Such compositions typically include the peptide and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with the intended route of administration. Routes of administration include, for example, parenteral (e.g., intravenous, intradermal, intraperitoneal or subcutaneous), oral, respiratory (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity, such as sodium chloride or dextrose. The pH can be adjusted with acids or bases, such as hydrochloric acid or sodium hydroxide. The preparation can be enclosed in ampoules, disposable syringes or multiple-dose vials made of glass or plastic. For convenience of the patient or treating physician, the dosing formulation can be provided in a kit containing all necessary equipment (e.g., vials of drug, vials of diluent, syringes and needles) for a course of treatment (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J., USA) or phosphate buffered saline (PBS). In all cases, a composition for parenteral administration must be sterile and should be formulated for ease of syringeability. The composition should be stable under the conditions of manufacture and storage, and must be shielded from contamination by microorganisms such as bacteria and fungi.

In one embodiment, the peptide or pharmaceutically acceptable salt thereof, of the present technology are administered intravenously. For example, an a peptide or pharmaceutically acceptable salt thereof, of the present technology may be administered via rapid intravenous bolus injection. In some embodiments, the peptide or pharmaceutically acceptable salt thereof, of the present technology is administered as a constant-rate intravenous infusion.

The peptide or pharmaceutically acceptable salt thereof, of the present technology may also be administered orally, topically, intranasally, intramuscularly, subcutaneously, or transdermally. In one embodiment, transdermal administration is by iontophoresis, in which the charged composition is delivered across the skin by an electric current.

Other routes of administration include intracerebroventricularly or intrathecally. Intracerebroventricularly refers to administration into the ventricular system of the brain. Intrathecally refers to administration into the space under the arachnoid membrane of the spinal cord. Thus, in some embodiments, intracerebroventricular or intrathecal administration is used for those diseases and conditions which affect the organs or tissues of the central nervous system.

The peptide or pharmaceutically acceptable salt thereof, of the present technology may also be administered to mammals by sustained release, as is known in the art. Sustained release administration is a method of drug delivery to achieve a certain level of the drug over a particular period of time. The level is typically measured by serum or plasma concentration. A description of methods for delivering a compound by controlled release can be found in international PCT Application No. WO 02/083106, which is incorporated herein by reference in its entirety.

Any formulation known in the art of pharmacy is suitable for administration of the peptide or pharmaceutically acceptable salt thereof, of the present technology. For oral administration, liquid or solid formulations may be used. Examples of formulations include tablets, gelatin capsules, pills, troches, elixirs, suspensions, syrups, wafers, chewing gum and the like. The peptide or pharmaceutically acceptable salt thereof, of the present technology can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the peptide or pharmaceutically acceptable salt thereof, of the present technology may utilize conventional diluents, carriers, or excipients etc., such as those known in the art to deliver the peptide or pharmaceutically acceptable salt thereof, of the present technology. For example, the formulations may comprise one or more of the following: a stabilizer, a surfactant, such as a nonionic surfactant, and optionally a salt and/or a buffering agent. The peptide or pharmaceutically acceptable salt thereof, of the present technology may be delivered in the form of an aqueous solution, or in a lyophilized form.

The stabilizer may comprise, for example, an amino acid, such as for instance, glycine; an oligosaccharide, such as, sucrose, tetralose, lactose; or a dextran. Alternatively, the stabilizer may comprise a sugar alcohol, such as, mannitol. In some embodiments, the stabilizer or combination of stabilizers constitutes from about 0.1% to about 10% weight for weight of the formulated composition.

In some embodiments, the surfactant is a nonionic surfactant, such as a polysorbate. Examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. In some embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

Formulations of peptide or pharmaceutically acceptable salt thereof, of the present technology may additionally contain one or more conventional additives. Examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; an anesthetic agent such as for example a morphine derivative; and an isotonic agent etc., such as described herein. As a further precaution against oxidation or other spoilage, the pharmaceutical compositions may be stored under nitrogen gas in vials sealed with impermeable stoppers.

The mammal treated in accordance with the present technology may be any mammal, including, for example, farm animals, such as sheep, pigs, cows, and horses; pet animals, such as dogs and cats; and laboratory animals, such as rats, mice and rabbits. In one embodiment, the mammal is a human.

The peptide or pharmaceutically acceptable salt thereof, of the present technology may be administered systemically or locally. In one embodiment, the peptide or pharmaceutically acceptable salt thereof, of the present technology are administered intravenously. For example, peptide or pharmaceutically acceptable salt thereof, of the present technology may be administered via rapid intravenous bolus injection. In one embodiment, the peptide or pharmaceutically acceptable salt thereof, of the present technology is administered as a constant-rate intravenous infusion.

The peptide or pharmaceutically acceptable salt thereof, of the present technology can be injected directly into a coronary artery during, for example, angioplasty or coronary bypass surgery, or applied onto coronary stents.

The peptide or pharmaceutically acceptable salt thereof, of the present technology may include a carrier, which can be a solvent or dispersion medium containing, for example, water, ethanol, polyol (for example, glycerol, propylene glycol, and liquid polyethylene glycol, and the like), or suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included in the composition to prevent oxidation. In many cases, it is desirable to include isotonic agents, for example, sugars, polyalcohols such as mannitol, sorbitol, or sodium chloride. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials may be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the peptide or pharmaceutically acceptable salt thereof, can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of peptide or pharmaceutically acceptable salt thereof, of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

Dosage, toxicity and therapeutic efficacy of the peptide or pharmaceutically acceptable salt thereof, of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the peptides or pharmaceutically acceptable salts thereof, of the present technology exhibit high therapeutic indices. While peptides or pharmaceutically acceptable salts thereof, of the present technology that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any peptide or pharmaceutically acceptable salt thereof, of the present technology used in the methods described herein, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the peptide or pharmaceutically acceptable salt thereof, of the present technology, sufficient for achieving a therapeutic or prophylactic effect, range from about 0.000001 mg per kilogram body weight per day to about 10,000 mg per kilogram body weight per day. In some embodiments, the dosage ranges will be from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide or pharmaceutically acceptable salt thereof, of the present technology ranges from 0.1-10,000 micrograms per kg body weight. In one embodiment, peptide or pharmaceutically acceptable salt thereof, concentrations in a carrier range from 0.2 to 2000 micrograms per delivered milliliter. An exemplary treatment regimen entails administration once per day or once a week. Intervals can also be irregular as indicated by measuring blood levels of glucose or insulin in the subject and adjusting dosage or administration accordingly. In some methods, dosage is adjusted to achieve a desired fasting glucose or fasting insulin concentration. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of peptide or pharmaceutically acceptable salt thereof, of the present technology is defined as a concentration of the peptide or pharmaceutically acceptable salt thereof, of the present technology at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses is optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and the presence of other diseases. Moreover, treatment of a subject with a therapeutically effective amount of the therapeutic compositions described herein can include a single treatment or a series of treatments.

VI. EXAMPLES

The present technology is further illustrated by the following examples, which should not be construed as limiting in any way. For each of the examples below, any peptide described herein could be used. By way of example, but not by limitation, the peptide used in the examples below could be selected from: D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$ (SBT-100), D-Orn-L-DMT-L-Lys-L-Phe-NH$_2$(SBT-131), D-(Amidine)Arg(propylamine)-L-DMT-L-Lys-L-Phe-NH$_2$(SBT-140), or D-Arg(butylamidine analog)-L-DMT-L-Lys-L-Phe-NH$_2$ (SBT-149).

Example 1: Effect of Peptides on Myocardial Function and Response to Reperfusion Injury This example will show that the peptides of the present technology are useful in the treatment of cardiac ischemic injury and cardiac ischemic-reperfusion injury.

Modified Langendorff Model

The Langendorff rodent heart model is widely employed in studies of myocardial function and responses to injury (e.g., ischemia). For whole-heart studies, male Sprague-Dawley rats (7-9 weeks old) were injected with pentobarbital (35 mg/kg, ip injection) and hearts were excised with midline thoracotomy. The aortas were secured around a cannula of a modified Langendorff apparatus and retrogradely perfused (perfusion pressure of 75 mm Hg) with a modified Krebs-Henseleit buffer containing (in mM): 118 NaCl, 24 NaHCO$_3$, 4.75 KCl, 1.2 KH$_2$PO$_4$, 1.2 MgSO$_4$, 2.0 CaCl$_2$, and 10 glucose (gassed with 95/5% O$_2$/CO$_2$). Hearts were bathed in a buffer-filled perfusion chamber maintained at 37° C. for the duration of the experiments. Following the initiation of perfusion, hearts were instrumented for the simultaneous observation of mechanical and electrical function. A buffer-filled latex balloon (size 5, Harvard Apparatus, Holliston, Mass., USA), calibrated at the beginning of each day using a digital manometer, was inserted into the left ventricle (via the mitral valve) for the measurement of left ventricular developed pressure (LVDP), with balloon volume adjusted to establish a diastolic pressure of 5-8 mm Hg. Three electrodes were placed into the buffer filled perfusion chamber for the measurement of the volume-conducted electrocardiogram (ECG). Coronary flow rates were monitored constantly with a flow probe (Transconic Systems, Ithaca, N.Y., USA) connected in series with the perfusion line, and normalized to heart wet weight (in grams) at the end of each experiment. All physiological parameters were continuously monitored and stored on a personal computer using commercially available software (Chart, AD Instruments, Colorado Springs, Colo., USA). Heart rate was calculated using the LVDP trace, and maximal rates of contraction(+dP/dt) and relaxation (−dP/dt) were calculated using the derivative of the LVDP trace.

Ischemia/Reperfusion Protocol and Peptide Treatments

Figure 1B:
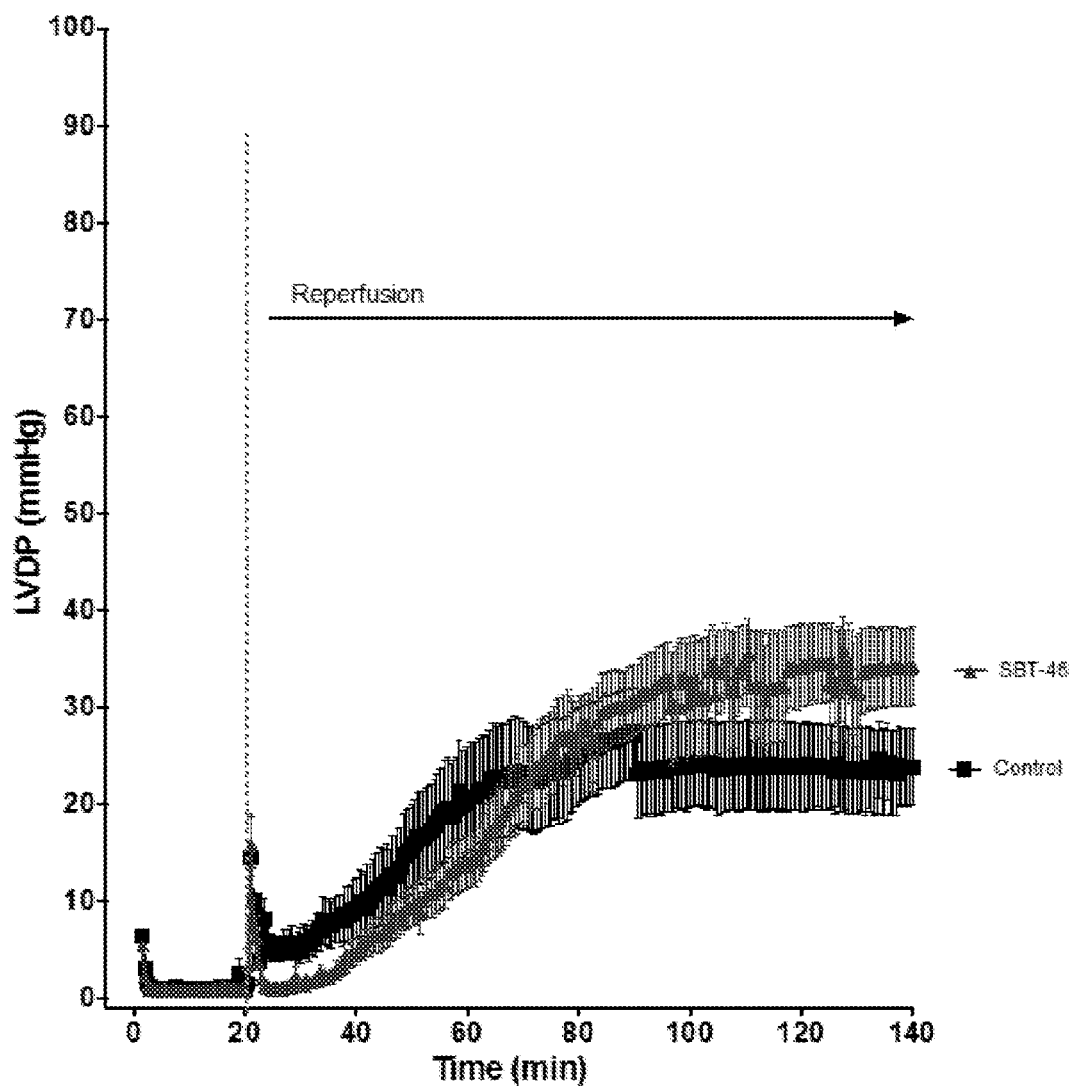
Figure 1C:
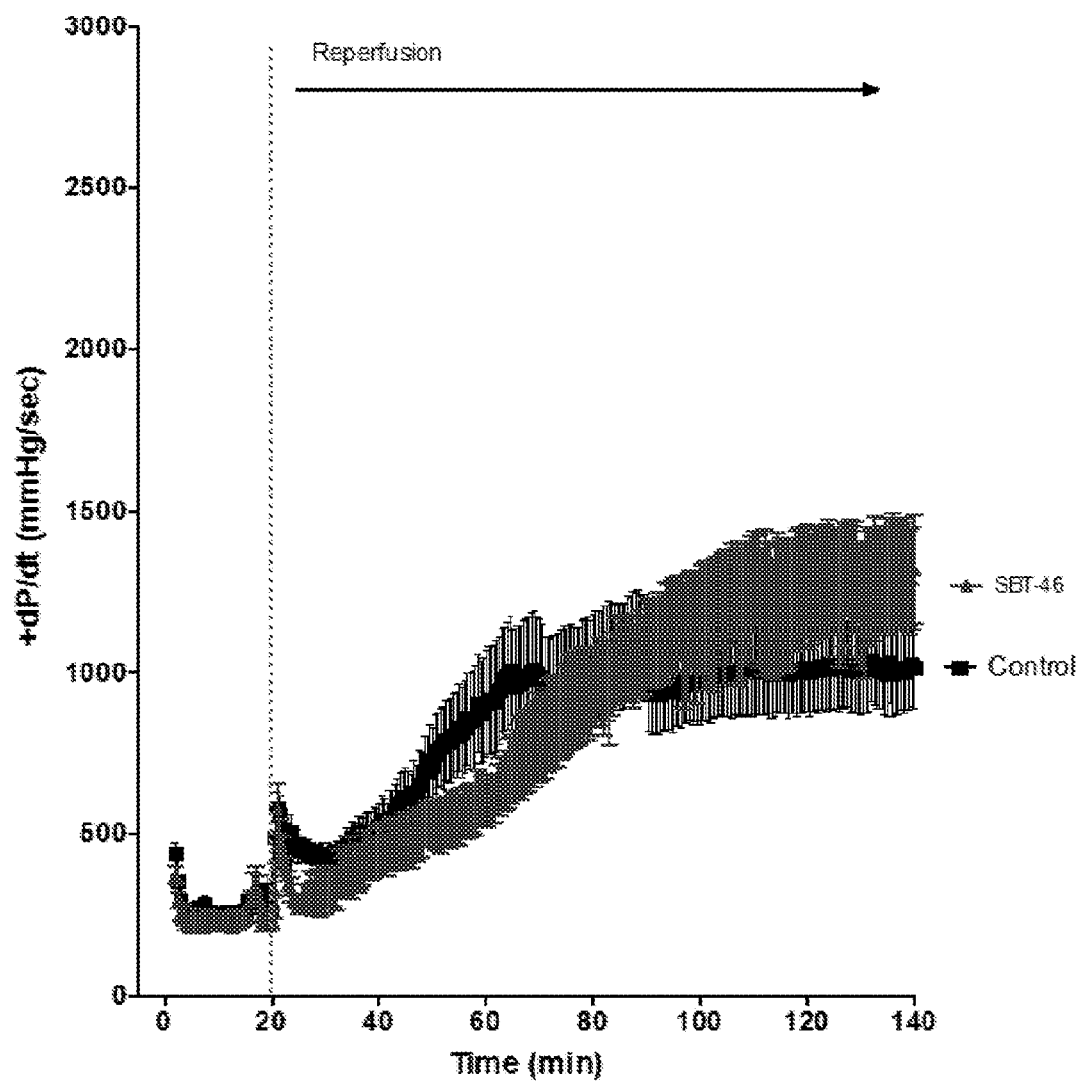
Figure 1D:
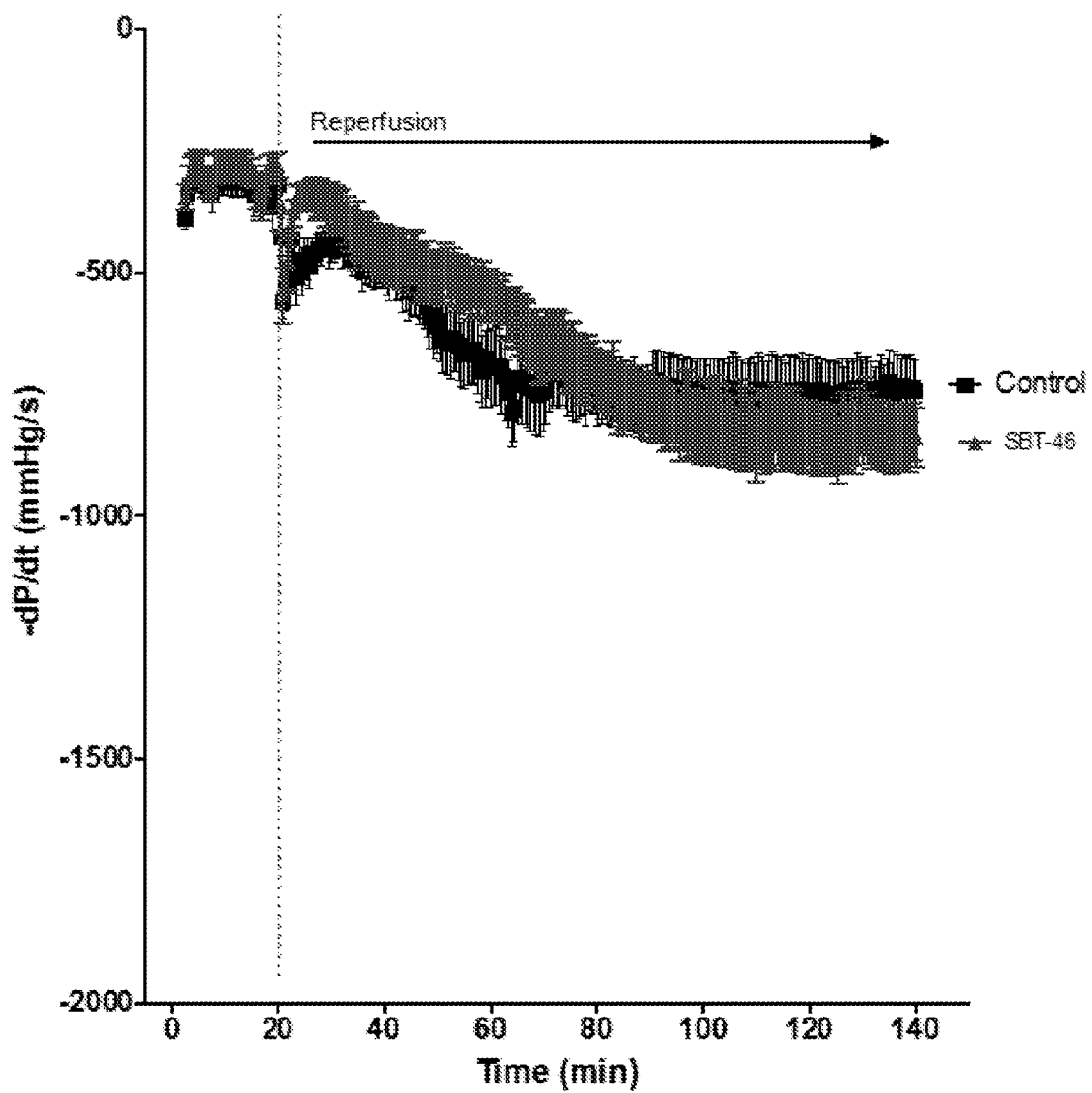
Figure 2A:
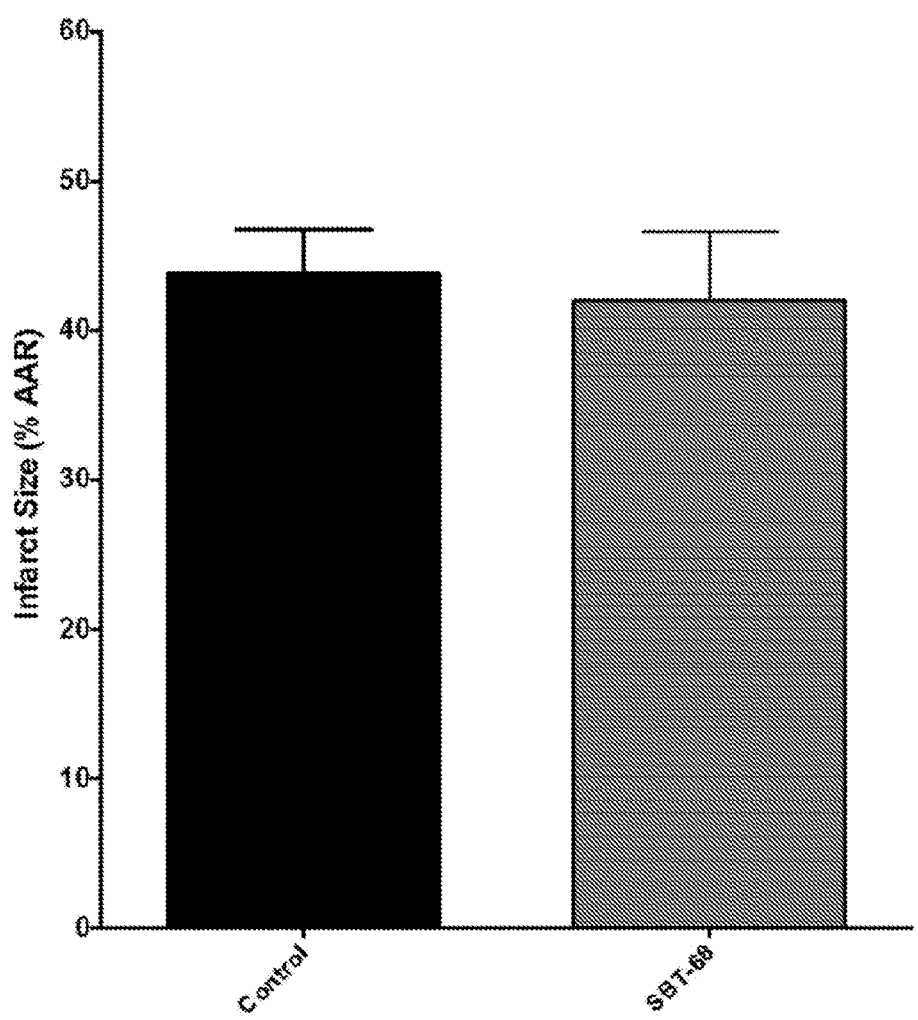
FIGS. 2A-D are graphs showing an illustrative example of attenuation of cardiac ischemia-reperfusion injury in a modified Langendorff rat heart model. Excised Sprague-Dawley rat hearts were reperfused as described in Example 1. Data is shown for infarct size expressed as a percentage of AAR (FIG. 2A), left ventricular developed pressure (LVDP) (FIG. 2B), and maximal rates of contraction and relaxation (±dP/dt) (FIGS. 2C-D) for control hearts and hearts treated with D-Arg-L-DMT-L-Ala-L-Phe-NH$_2$ (SBT-68).
Figure 2B:
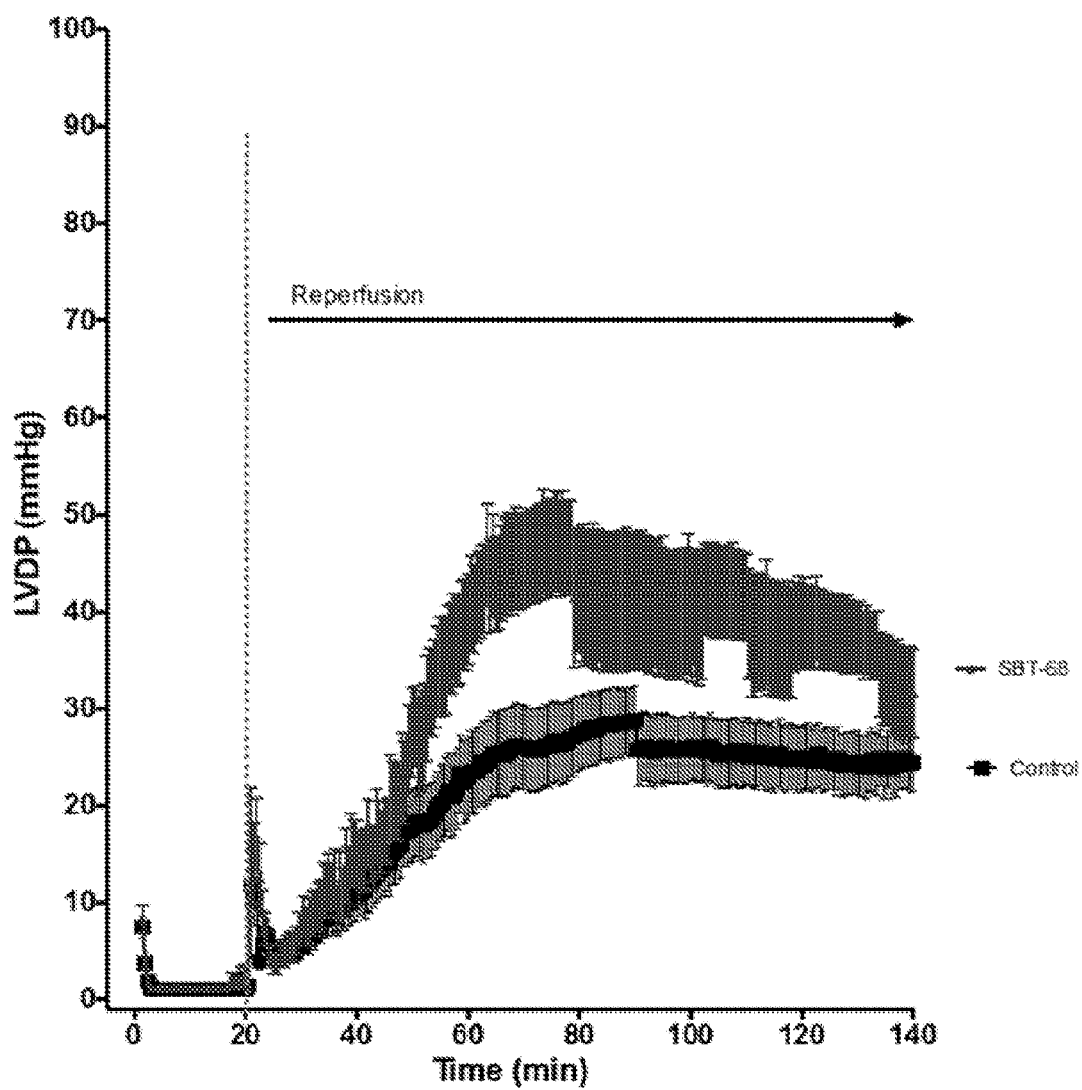
Figure 2C:
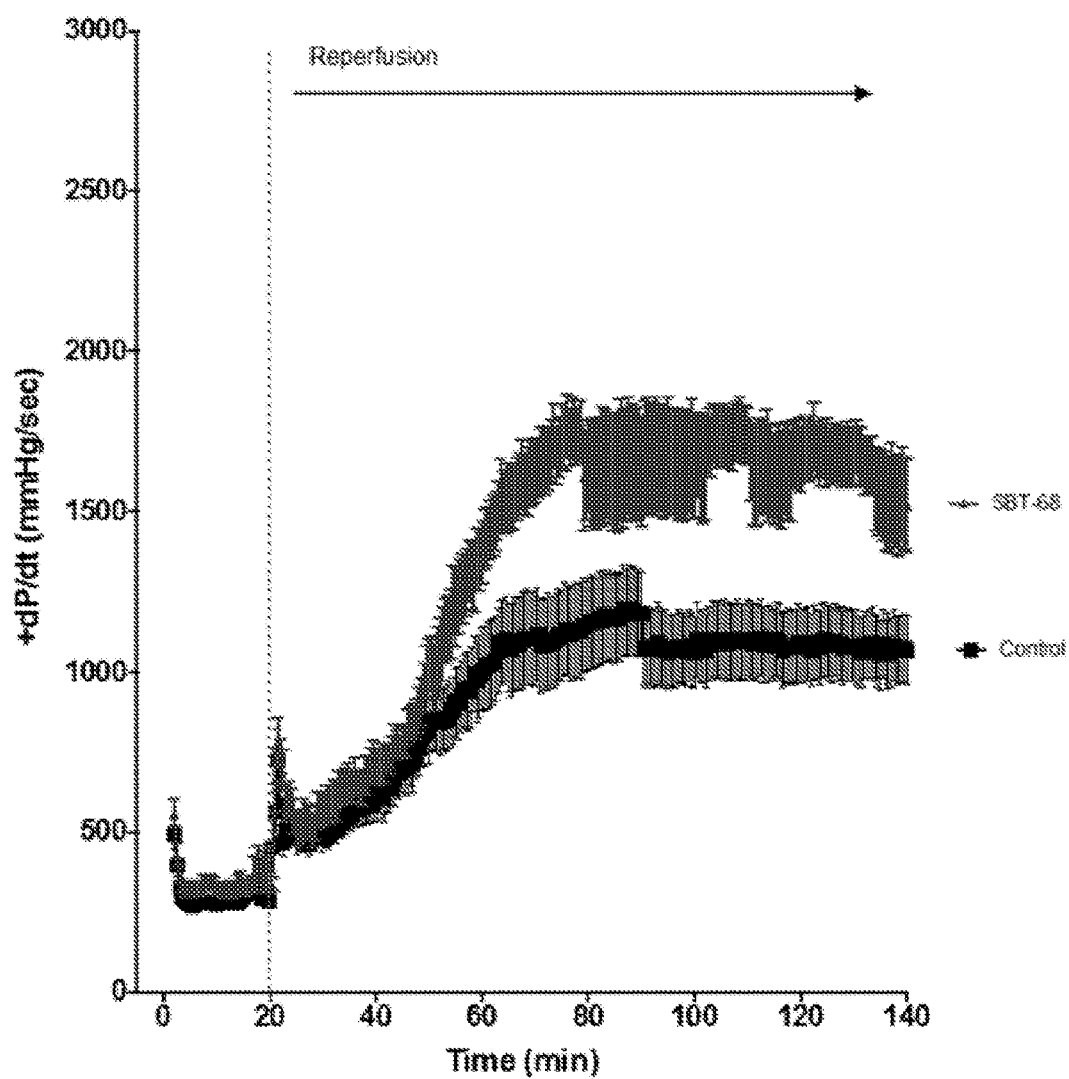
Figure 2D:
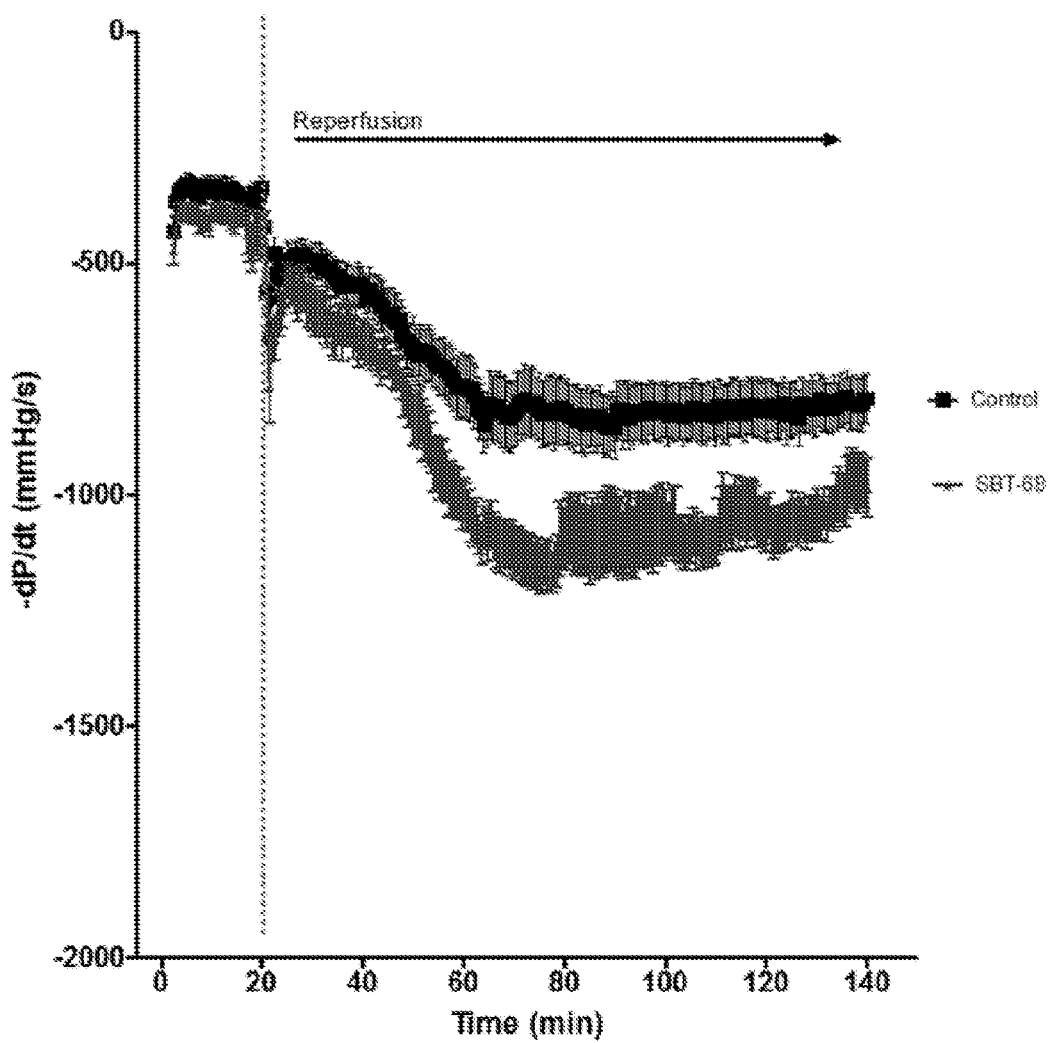
Figure 3A:
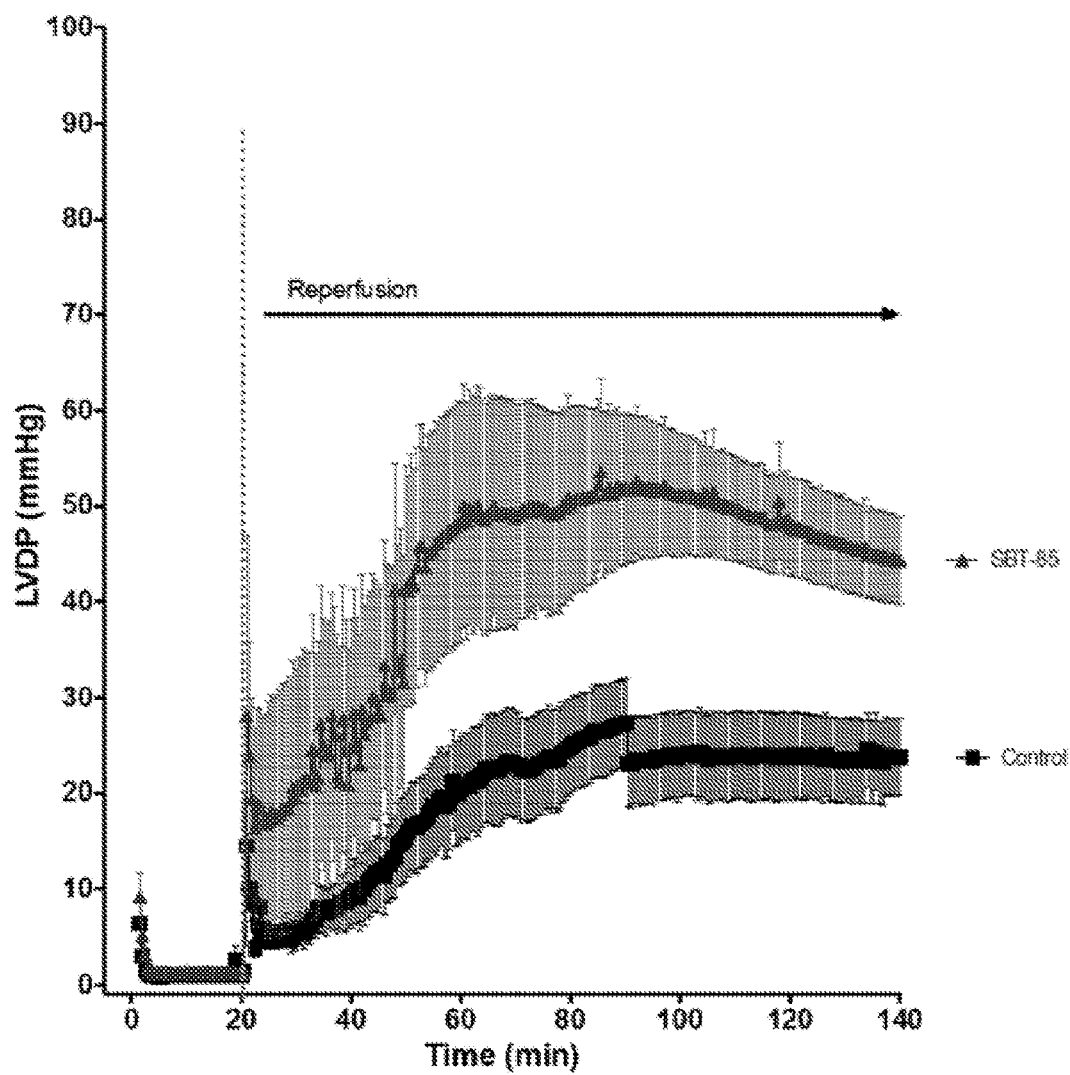
FIGS. 3A-C are graphs showing an illustrative example of attenuation of cardiac ischemia-reperfusion injury in a modified Langendorff rat heart model. Excised Sprague-Dawley rat hearts were reperfused as described in Example 1. Data is shown for left ventricular developed pressure (LVDP) (FIG. 3A), and maximal rates of contraction and relaxation (±dP/dt) (FIGS. 3B-C) for control hearts and hearts treated with (Ac)-D-Arg-L-DMT-L-Lys-L-Phe-NH$_2$ (SBT-85).
Figure 3B:
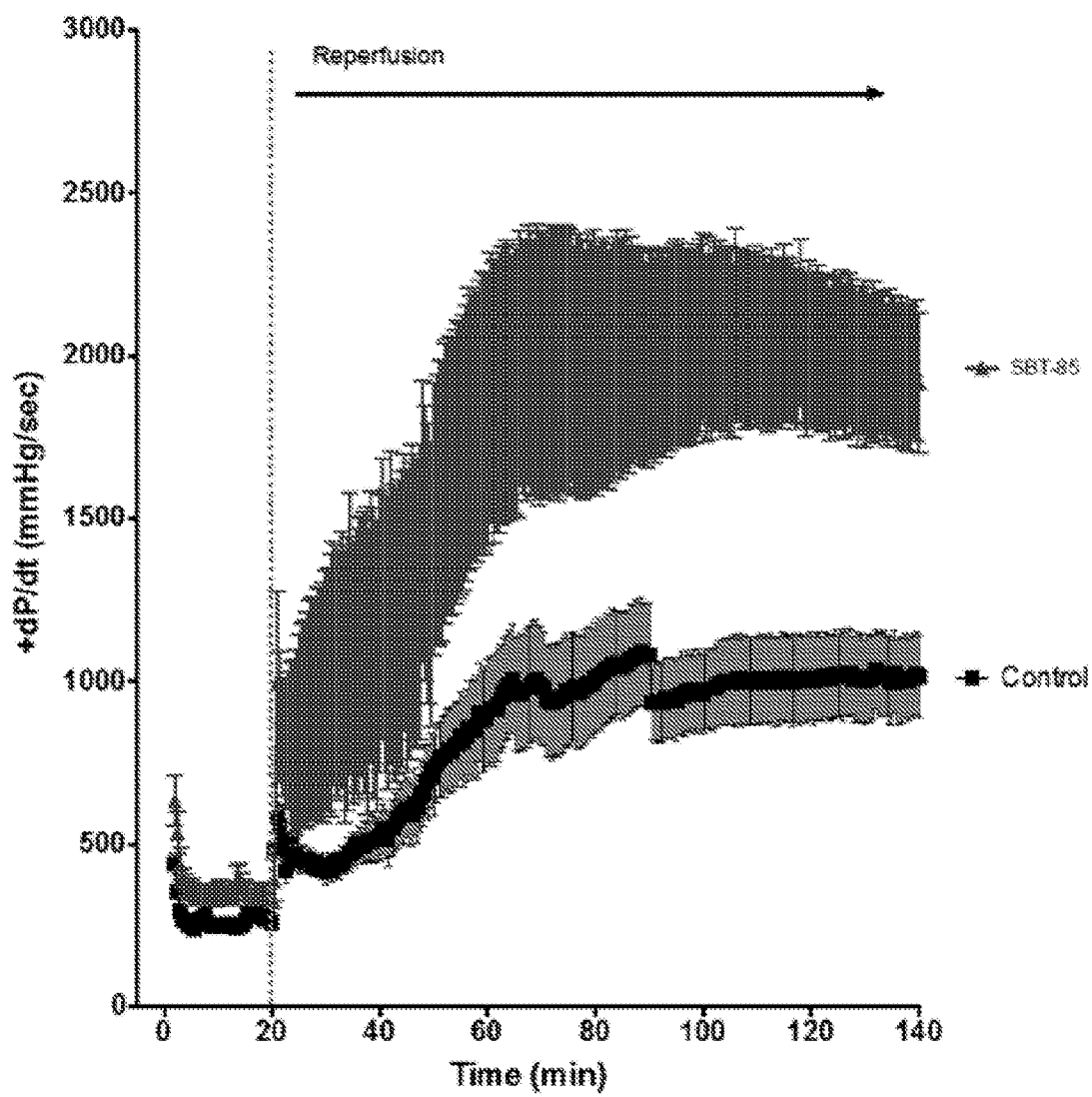
Figure 3C:
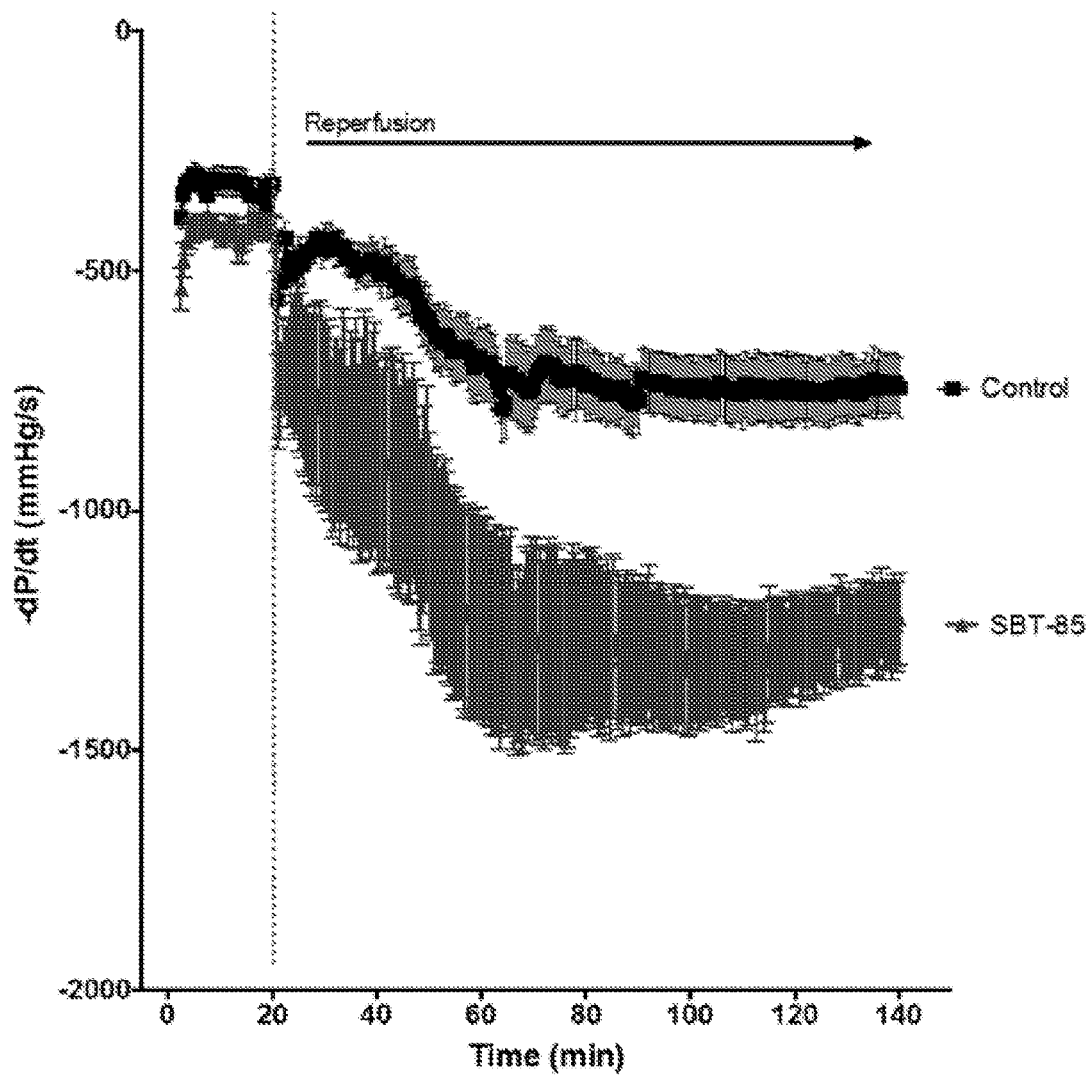
Figure 4A:
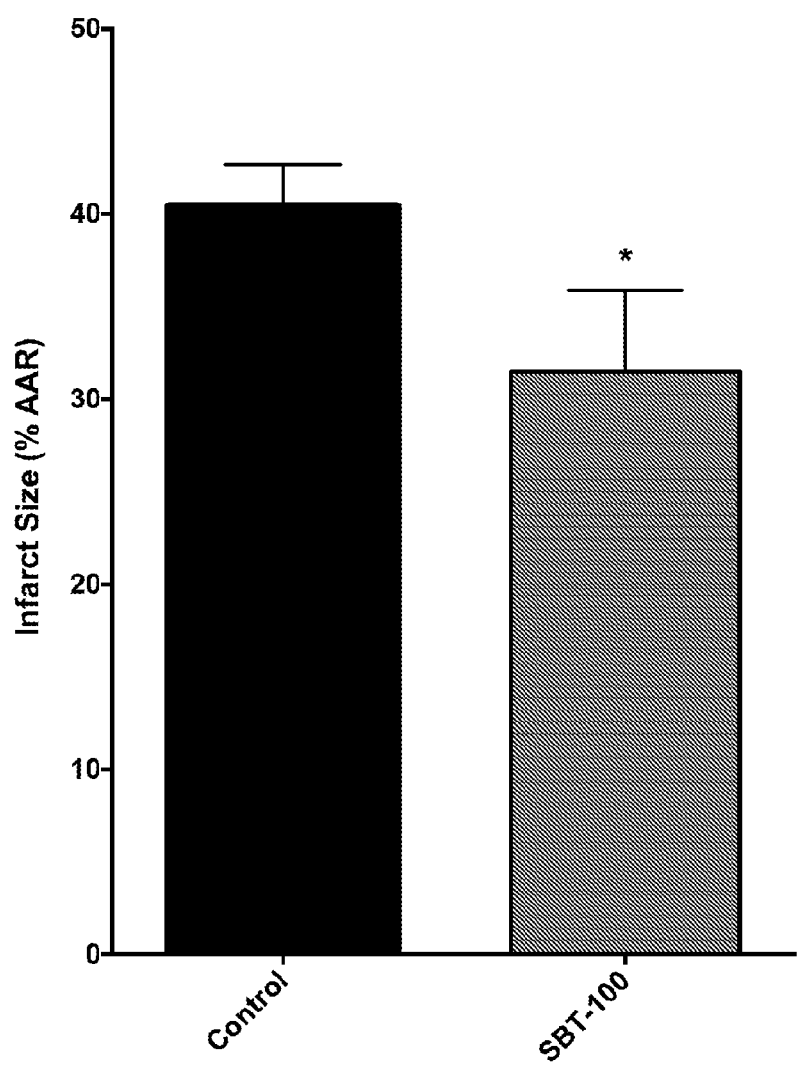
FIGS. 4A-D are graphs showing an illustrative example of attenuation of cardiac ischemia-reperfusion injury in a modified Langendorff rat heart model. Excised Sprague- Dawley rat hearts were reperfused as described in Example 1. Data is shown for infarct size expressed as a percentage of AAR (FIG. 4A), left ventricular developed pressure (LVDP) (FIG. 4B), and maximal rates of contraction and relaxation (±dP/dt) (FIGS. 4C-D) for control hearts and hearts treated with D-Arg-L-Dmt-L-His-L-Phe-$NH_2$ (SBT-100).
Figure 4B:
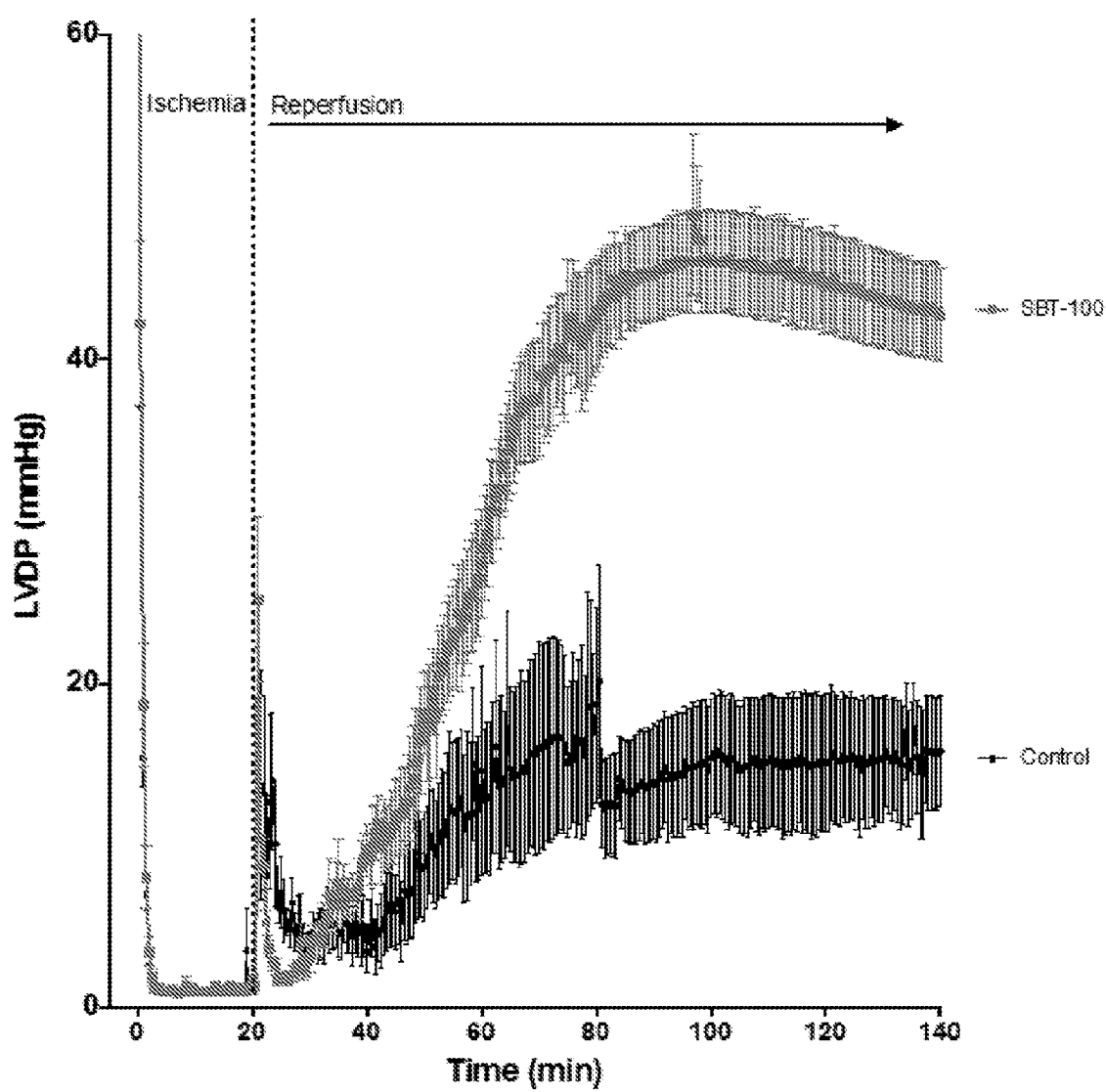
Figure 4C:
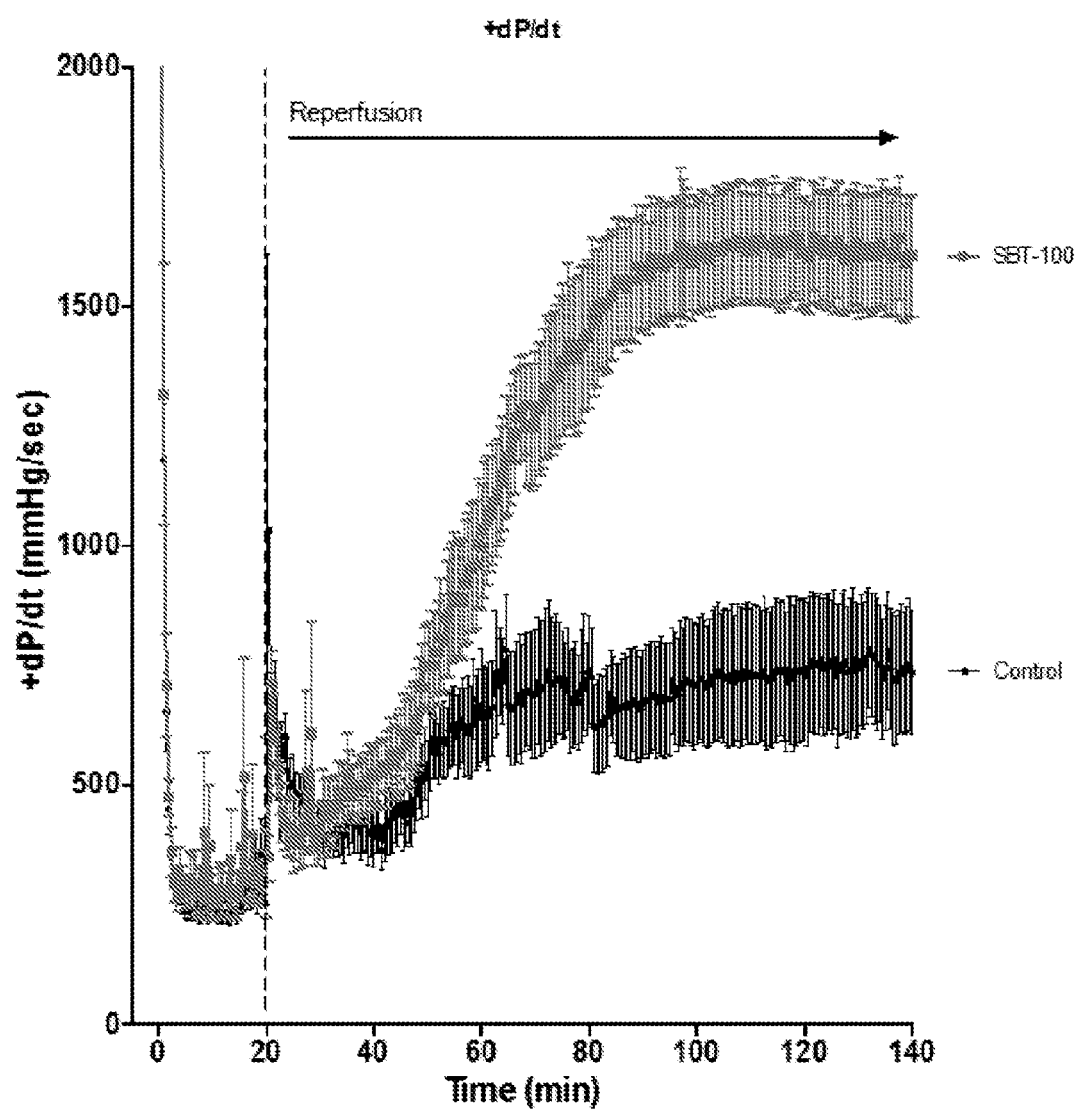
Figure 4D:
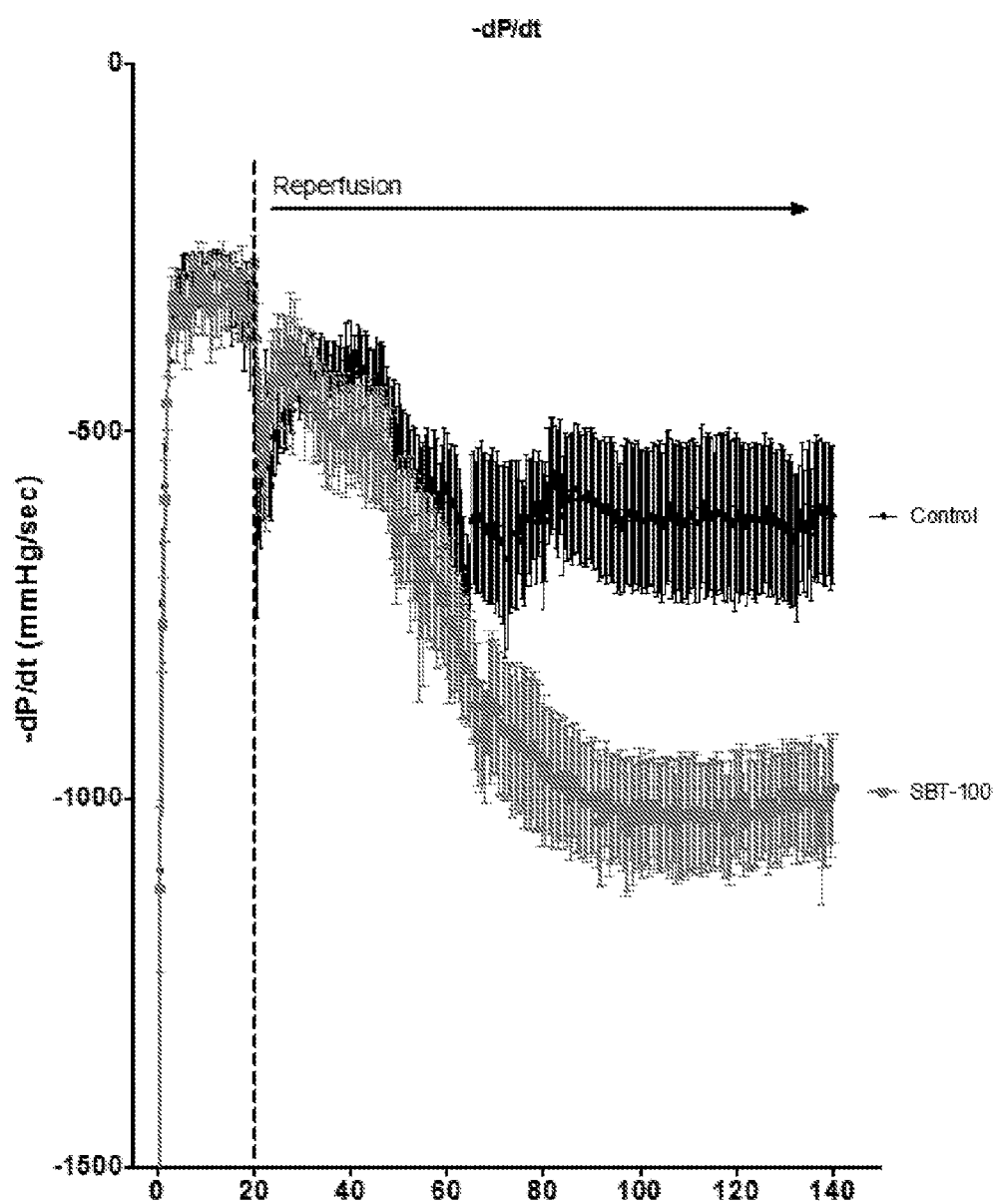
Figure 5A:
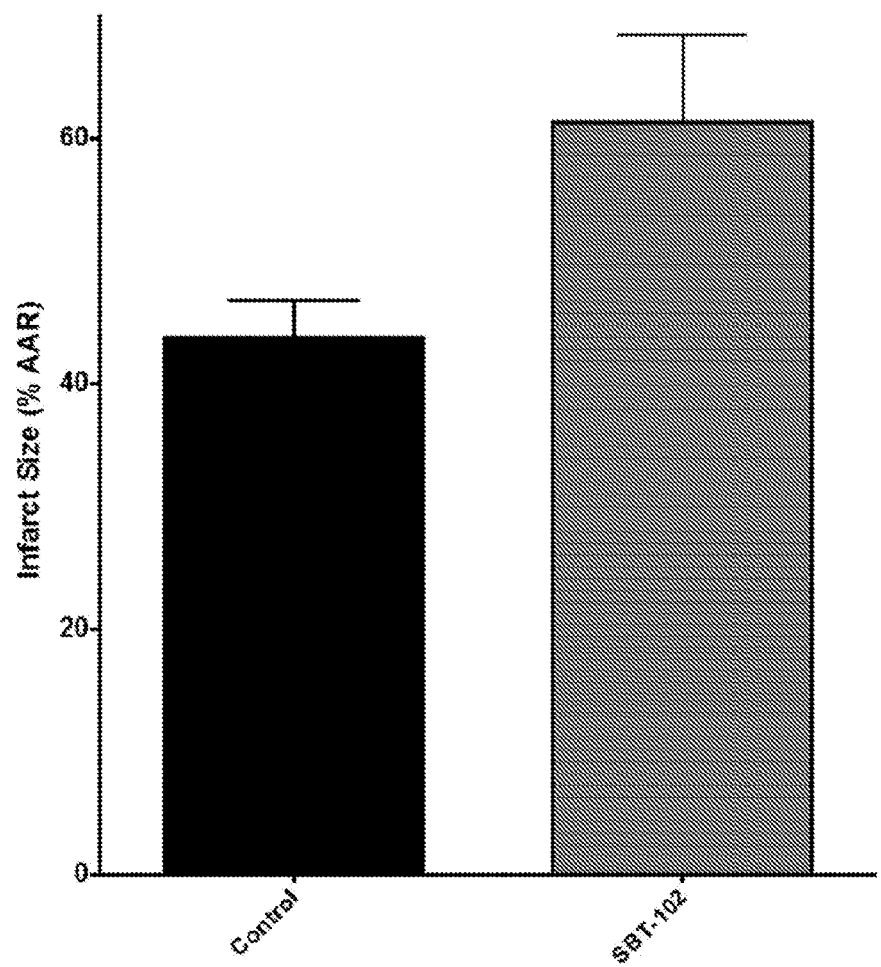
Figure 5B:
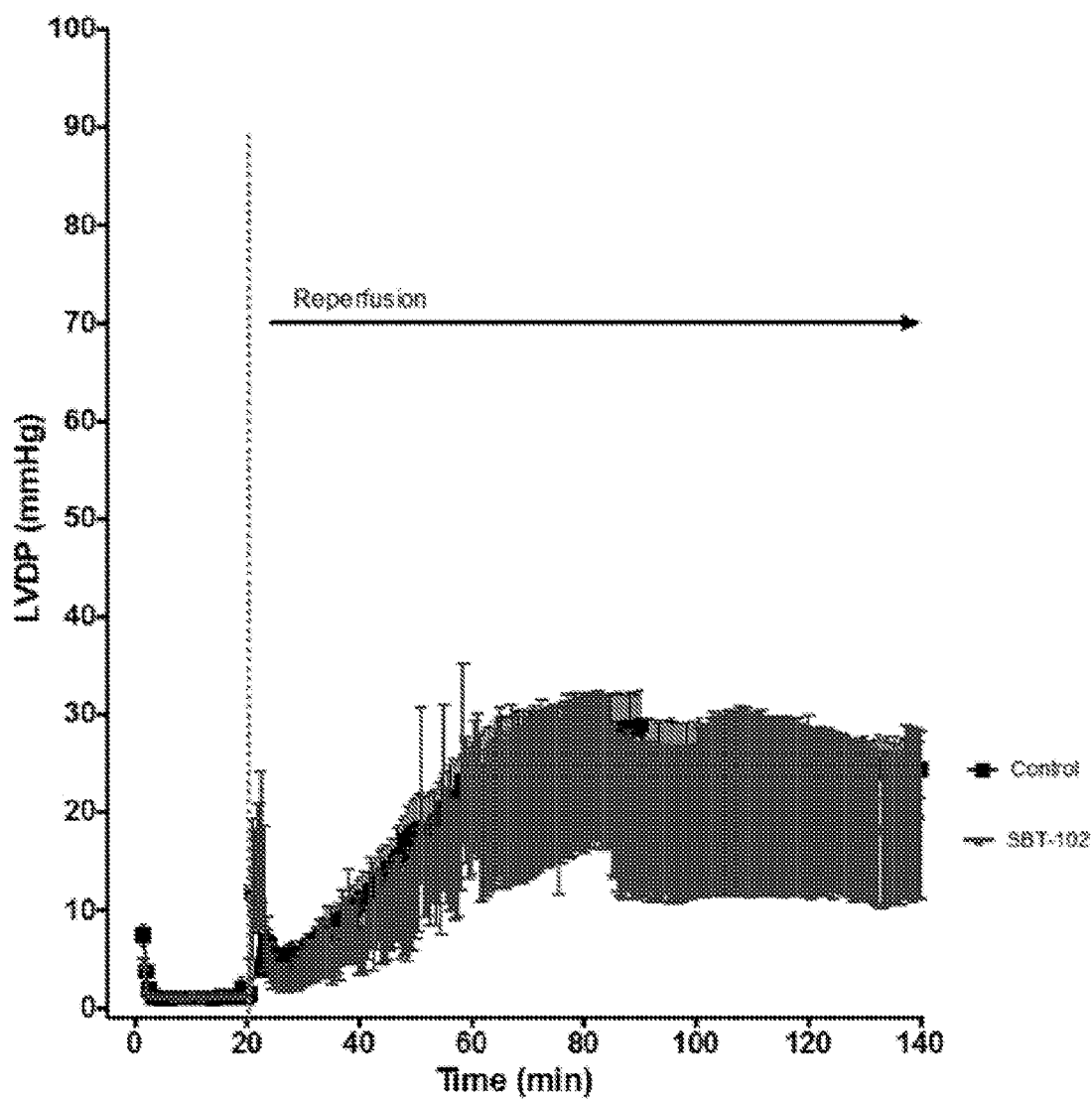
Figure 5D:
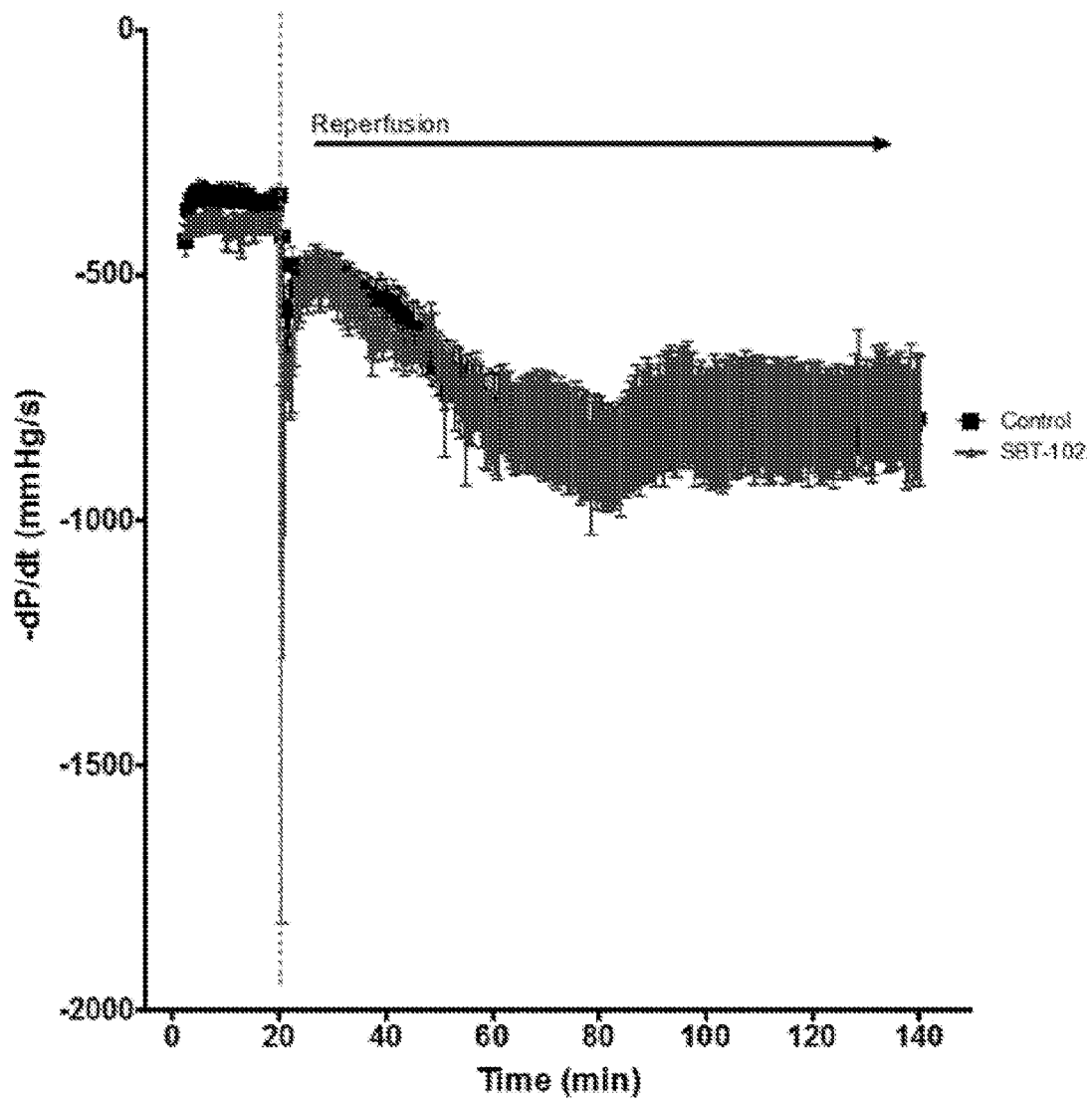
Figure 6A:
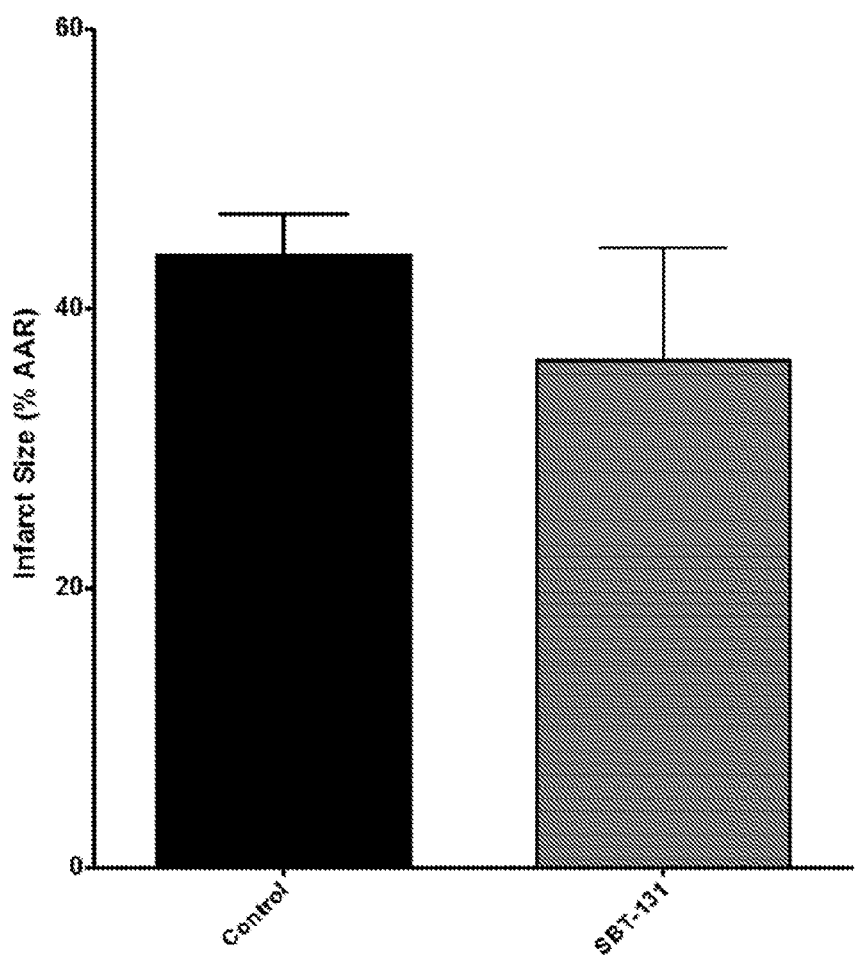
FIGS. 6A-D are graphs showing an illustrative example of attenuation of cardiac ischemia-reperfusion injury in a modified Langendorff rat heart model. Excised Sprague-Dawley rat hearts were reperfused as described in Example 1. Data is shown for infarct size expressed as a percentage of AAR (FIG. 6A), left ventricular developed pressure (LVDP) (FIG. 6B), and maximal rates of contraction and relaxation (±dP/dt) (FIGS. 6C-D) for control hearts and hearts treated with D-Orn-L-DMT-L-Lys-L-Phe-$NH_2$(SBT-131).
Figure 6B:
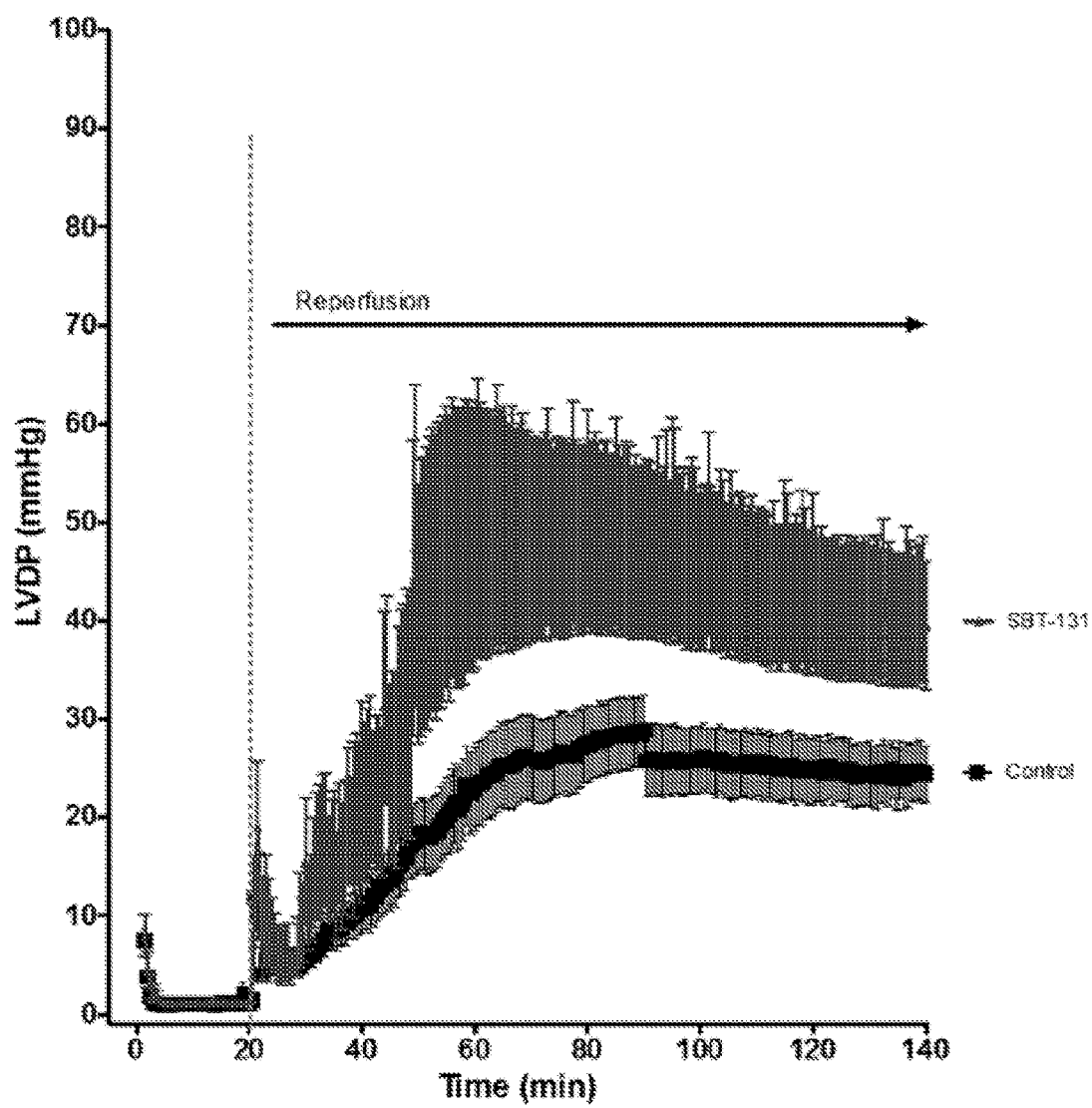
Figure 6C:
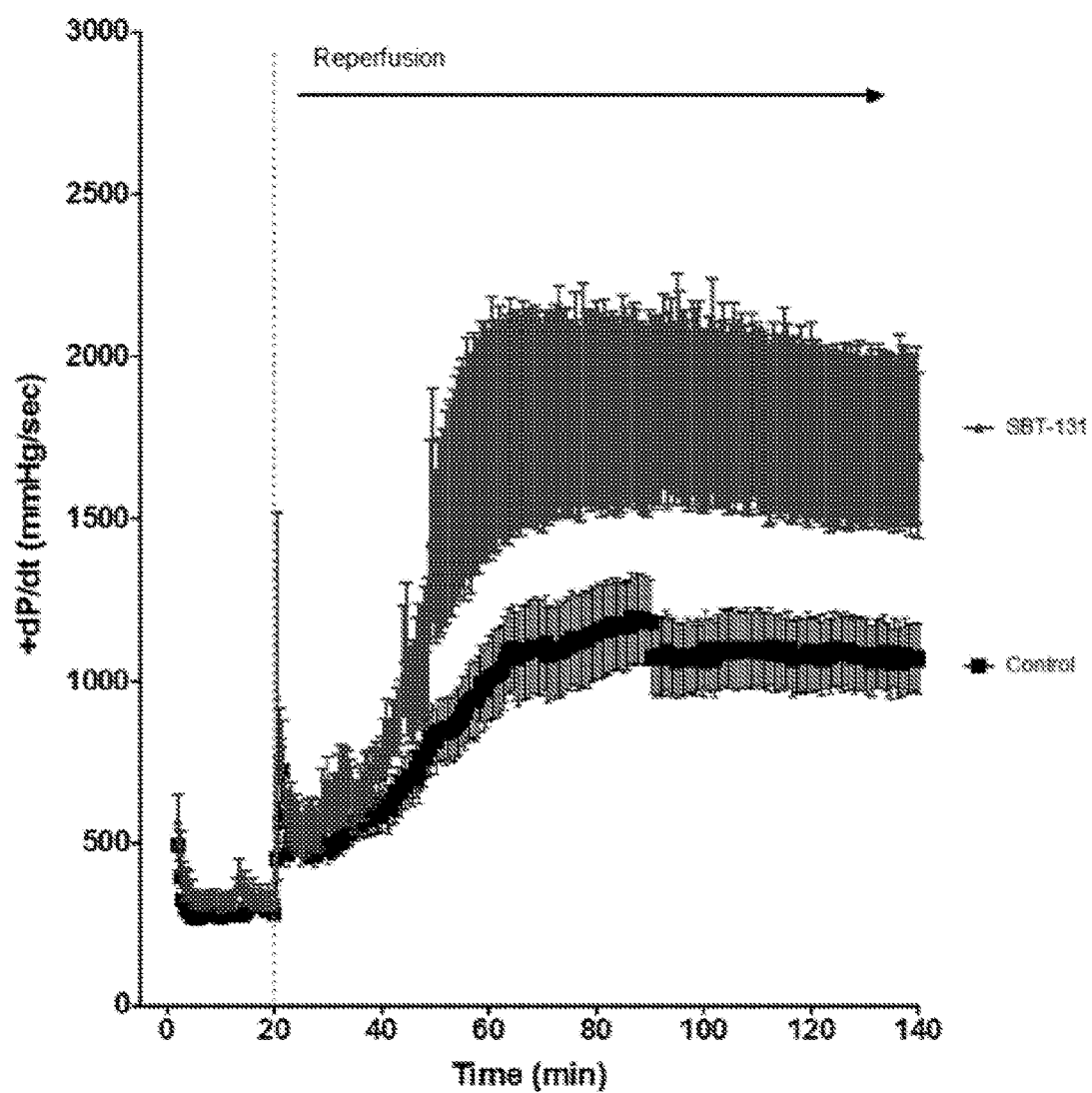
Figure 6D:
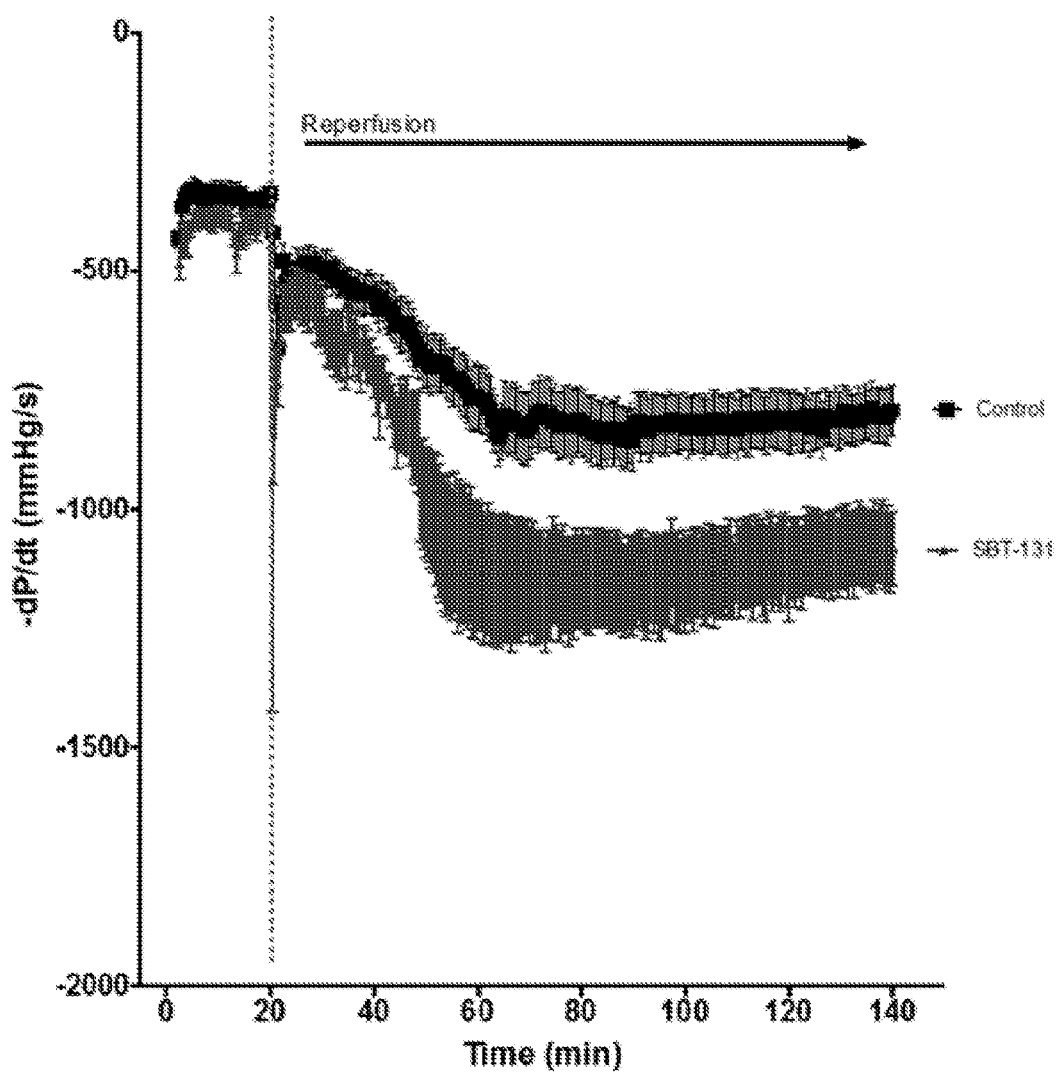
Figure 7A:
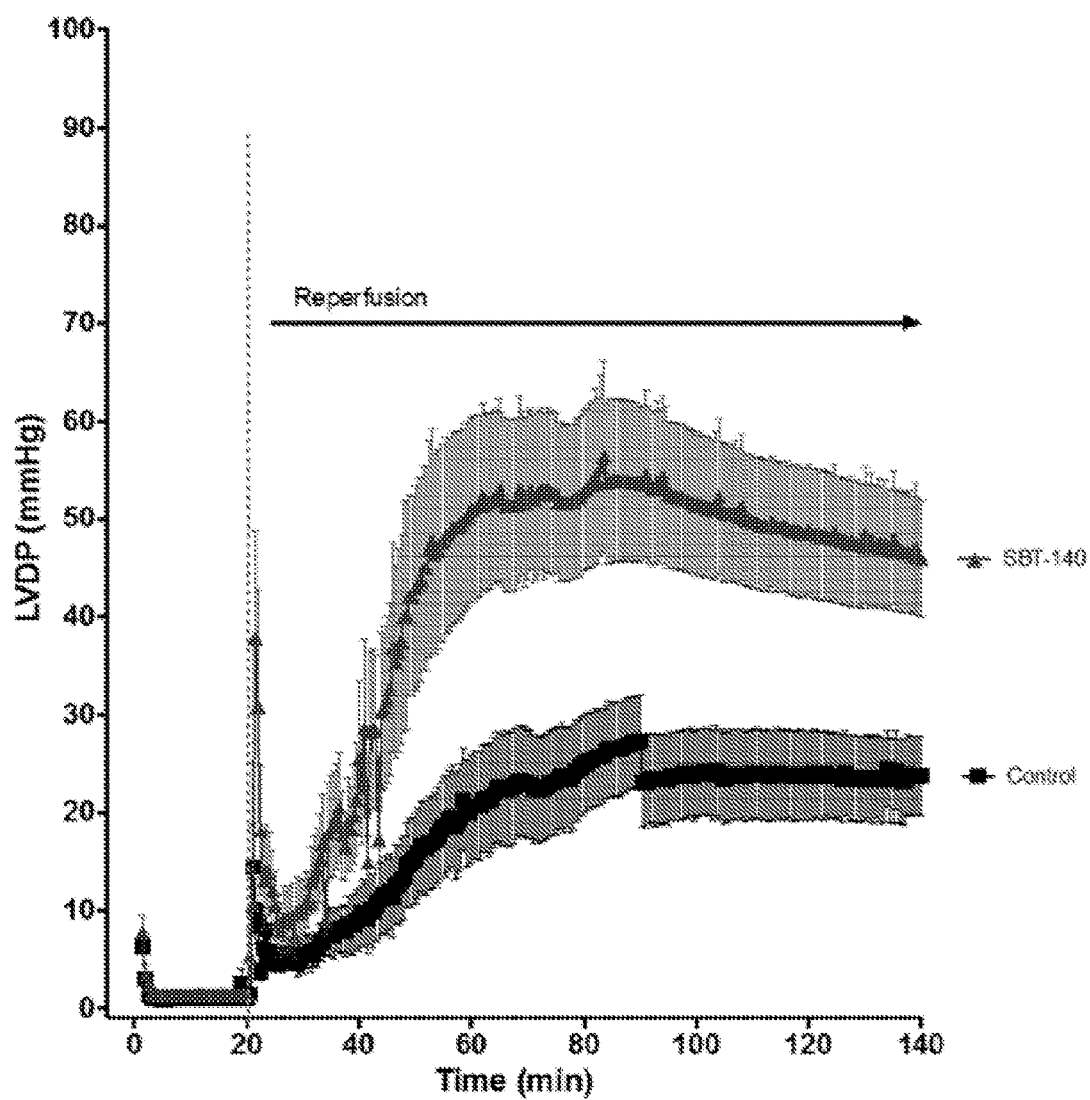
FIGS. 7A-C are graphs showing an illustrative example of attenuation of cardiac ischemia-reperfusion injury in a modified Langendorff rat heart model. Excised Sprague-Dawley rat hearts were reperfused as described in Example 1. Data is shown for left ventricular developed pressure (LVDP) (FIG. 7A), and maximal rates of contraction and relaxation (±dP/dt) (FIGS. 7B-C) for control hearts and hearts treated with D-(Amidine)Arg(propylamine)-L-DMT-L-Lys-L-Phe-$NH_2$(SBT-140).
Figure 7B:
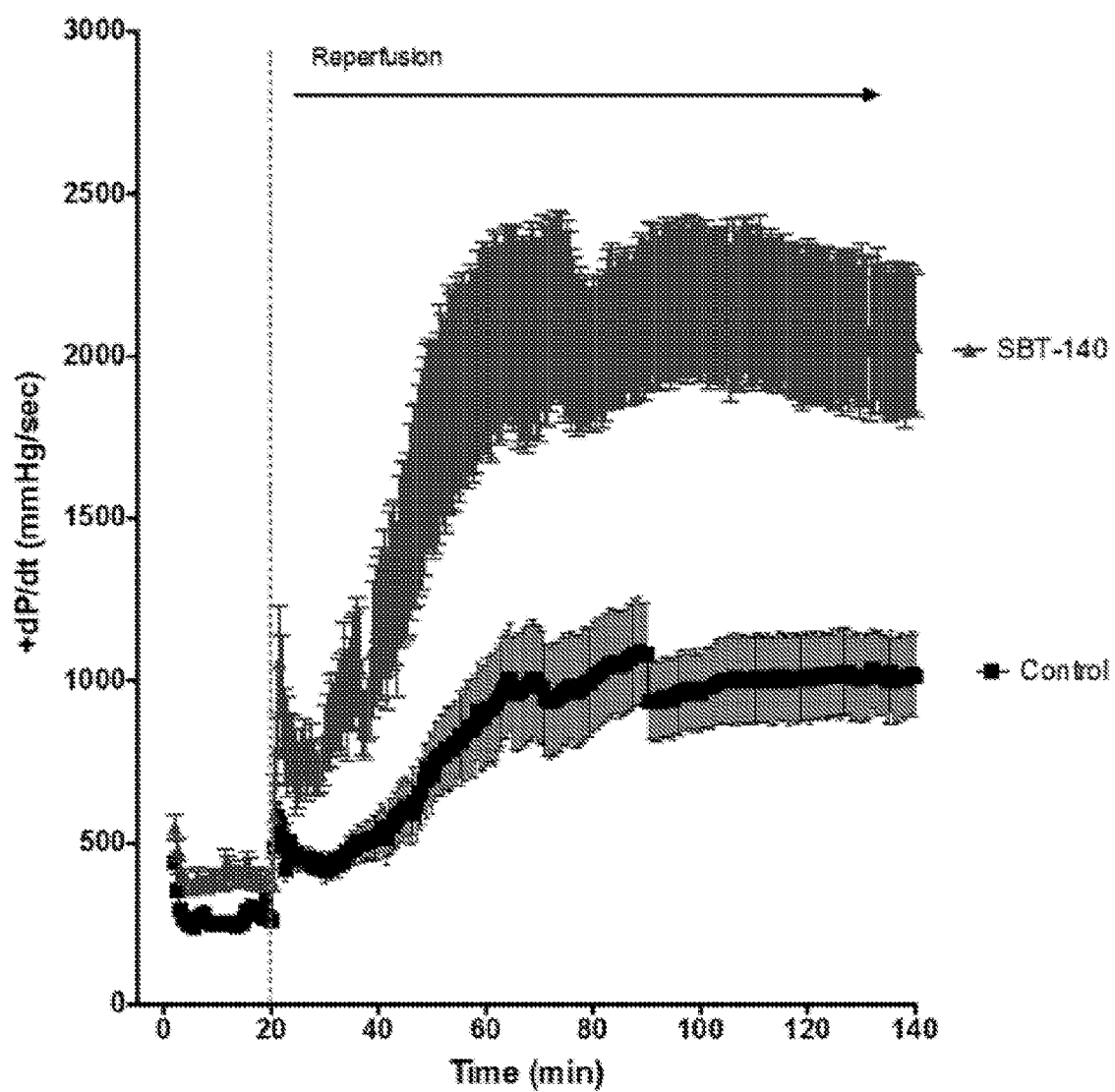
Figure 7C:
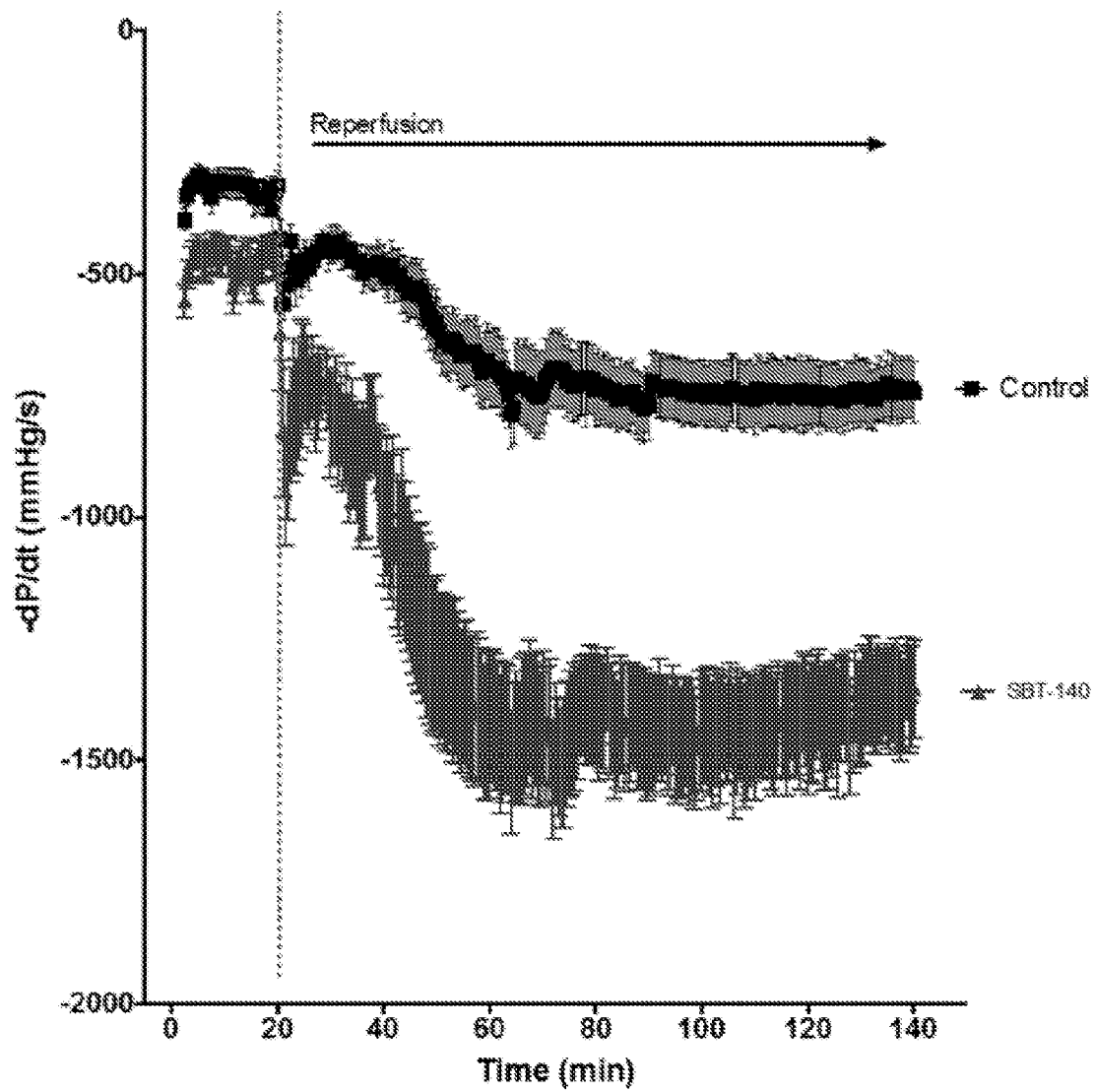
Figure 8A:
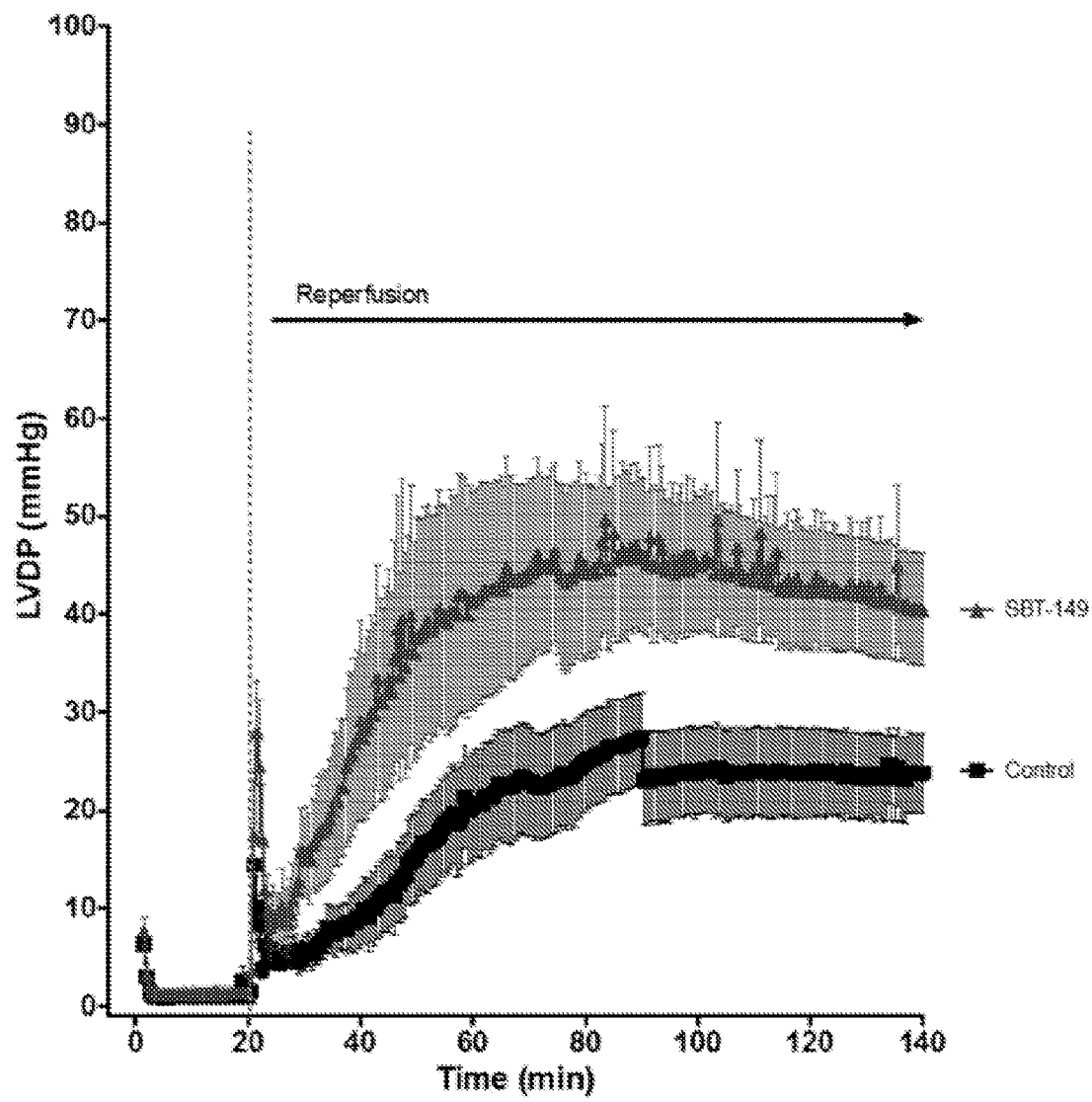
FIGS. 8A-C are graphs showing an illustrative example of attenuation of cardiac ischemia-reperfusion injury in a -modified Langendorff rat heart model. Excised Sprague-Dawley rat hearts were reperfused as described in Example 1. Data is shown for left ventricular developed pressure (LVDP) (FIG. 8A), and maximal rates of contraction and relaxation (±dP/dt) (FIGS. 8B-C) for control hearts and hearts treated with D-Arg(butylamidine analog)-L-DMT-L-Lys-L-Phe-$NH_2$(SBT-149).
Figure 8B:
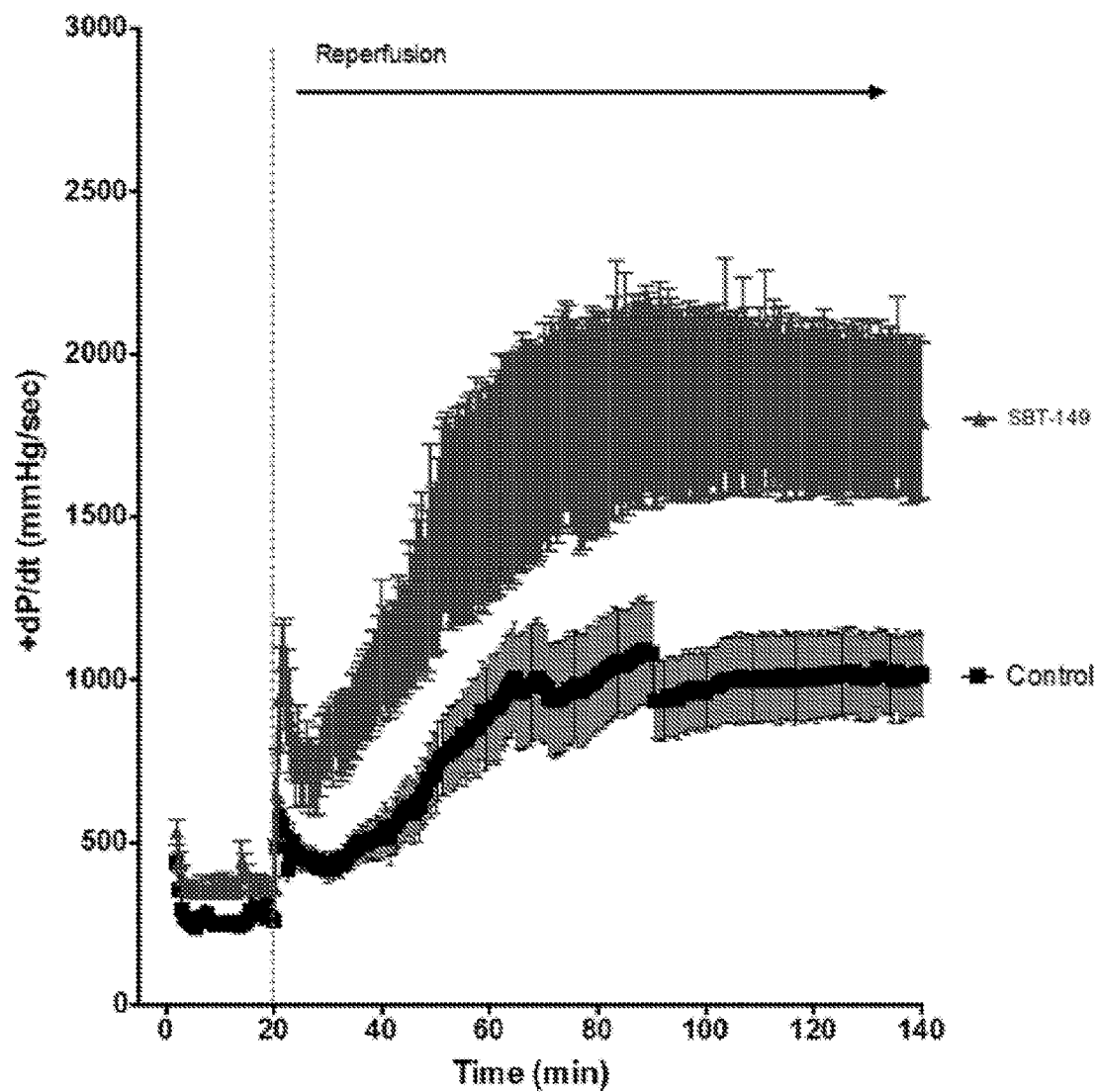
Figure 8C:
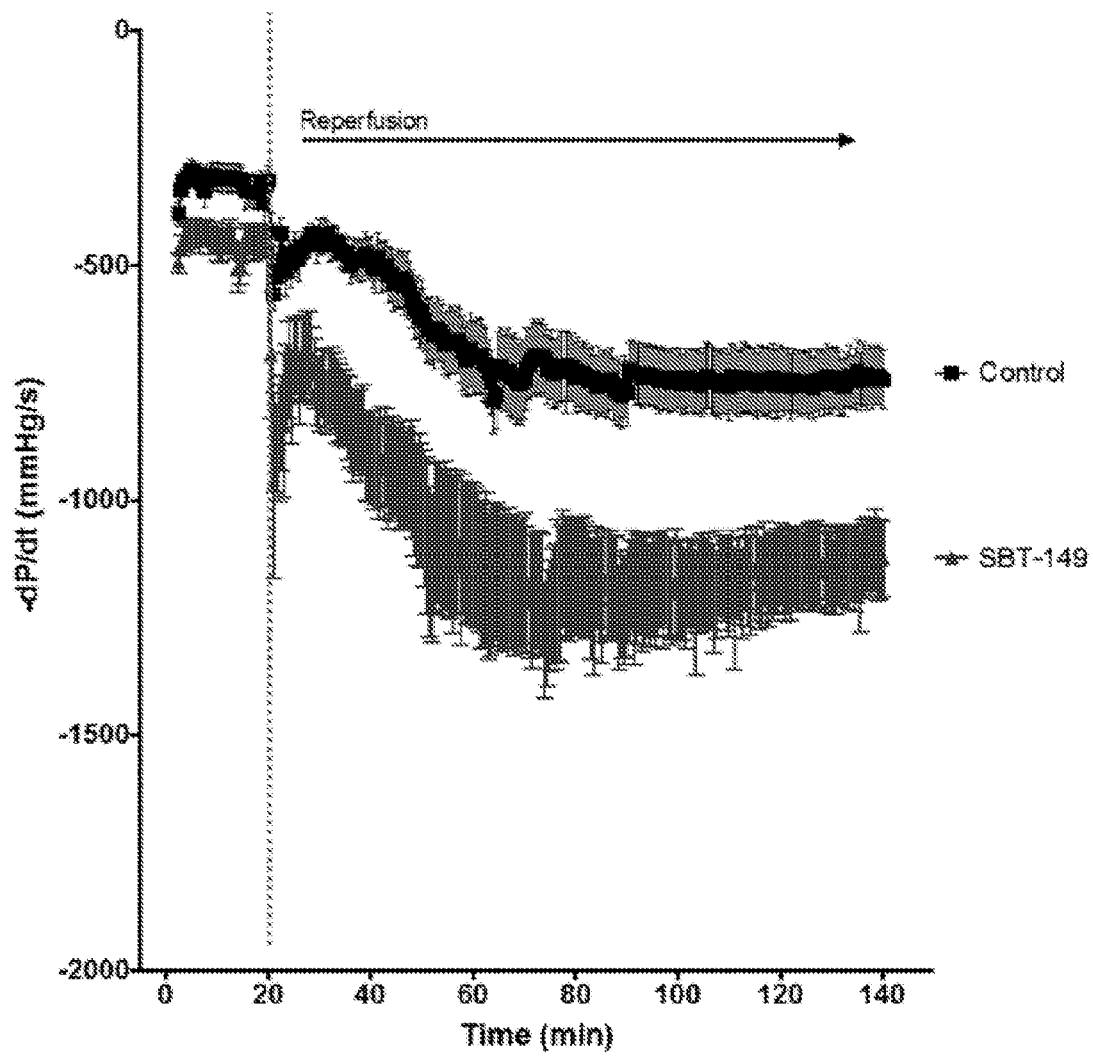
Figure 9:
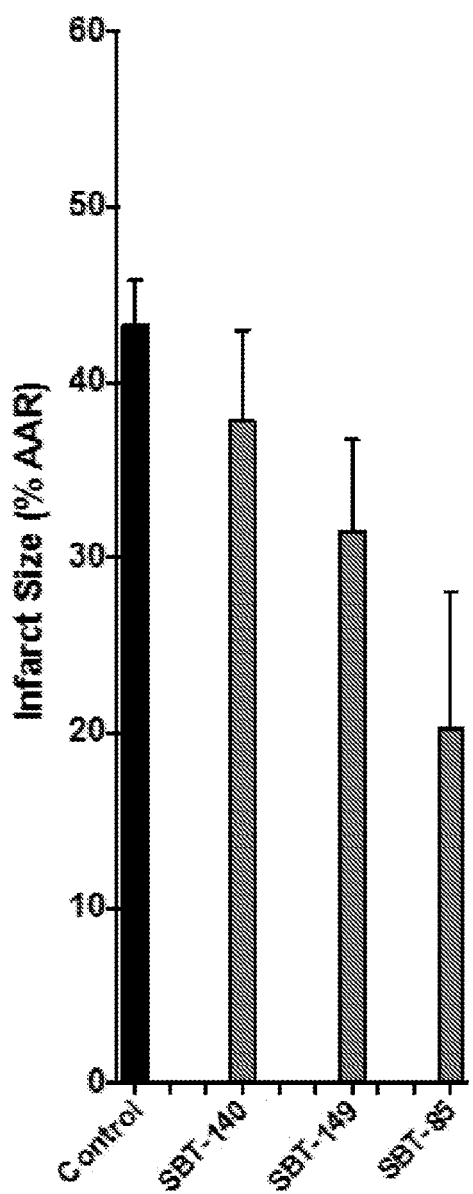
FIG. 9 is a graph showing the reduced infarct size expressed as a percentage of AAR for control Sprague-Dawley rat hearts and Sprague-Dawley rat hearts treated with (Ac)-D-Arg-L-DMT-L-Lys-L-Phe-$NH_2$ (SBT-85), D-(Amidine)Arg(propylamine)-L-DMT-L-Lys-L-Phe-$NH_2$ (SBT-140), or D-Arg(butylamidine analog)-L-DMT-L-Lys-L-Phe-$NH_2$ (SBT-149).

Following a 10 minute baseline period, ischemia/reperfusion was initiated. Hearts were exposed to global no-flow ischemia by stopping perfusion for 20 min. At the end of the index ischemia, static buffer from the perfusion lines was washed out (via an accessory port proximal to the aortic cannula), and reperfusion ensued for 2 hours either with Krebs buffer alone (control) or Krebs buffer containing an experimental peptide at a concentration of 1 µM. Peptides tested included D-Arg-D-Dmt-D-Lys-L-Phe-NH$_2$ (SBT-46), D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Arg-L-DMT-L-Orn-L-Phe-NH$_2$ (SBT-102), D-Orn-L-DMT-L-Lys-L-Phe-NH$_2$(SBT-131), D-(Amidine)Arg(propylamine)-L-DMT-L-Lys-L-Phe-NH$_2$ (SBT-140), and D-Arg(butylamidine analog)-L-DMT-L-Lys-L-Phe-NH$_2$(SBT-149). At the end of reperfusion, the left ventricle was dissected, sliced into 5 mm-thick slices, incubated in 1% triphenyltetrazolium chloride (TTC) for 10 min (37° C.) and digitally photographed for subsequent infarct size analysis. Infarct size was expressed as a percentage of the left ventricle (% area at risk (AAR))(calculated using ImageJ software, NIH, Bethesda, Md., USA).
Results Results for infarct size expressed as a percentage of AAR, LVDP, and maximal rates of contraction and relaxation (±dP/dt) for control and tested peptide (i.e., D-Arg-D-Dmt-D-Lys-L-Phe-NH$_2$(SBT-46), D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), Arg-DMT-Orn-Phe-NH$_2$ (SBT-102), D-Orn-L-DMT-L-Lys-L-Phe-NH$_2$(SBT-131), D-(Amidine)Arg(propylamine)-L-DMT-L-Lys-L-Phe-NH$_2$(SBT-140), and D-Arg (butylamidine analog)-L-DMT-L-Lys-L-Phe-NH$_2$ (SBT-149)) are shown in FIGS. 1-9.

The results show that treatment with D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$ (SBT-100), D-Orn-L-DMT-L-Lys-L-Phe-NH$_2$(SBT-131), D-(Amidine)Arg(propylamine)-L-DMT-L-Lys-L-Phe-NH$_2$ (SBT-140), and D-Arg(butylamidine analog)-L-DMT-L-Lys-L-Phe-NH$_2$ (SBT-149) was able to attenuate cardiac ischemia injury and ischemia-reperfusion injury as treatment with the peptides reduced infarct size (see FIGS. 2A, 4A, 6A, and 9), increased LVDP (see FIGS. 2B, 3A, 4B, 6B, 7A, and 8A), increased maximal rates of contraction (+dP/dt) (see FIGS. 2C, 3B, 4C, 6C, 7B, and 8B), and increased maximal rates of relaxation (−dP/dt) (see FIGS. 2D, 3C, 4D, 6D, 7C, and 8C) as compared to controls.

The results also show that treatment with select peptides of the present technology can attenuate cardiac ischemia injury and ischemia-reperfusion injury as treatment with the D-Arg-D-Dmt-D-Lys-L-Phe-NH$_2$ (SBT-46) and D-Arg-L-DMT-L-Orn-L-Phe-NH$_2$ (SBT-102) did not reduce infarct size, increase LVDP, or increase the maximal rates of contraction and relaxation (±dP/dt) (see FIGS. 1A-D and 5A-D) as compared to controls.

The results show that D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$ (SBT-131), D-(Amidine)Arg(propylamine)-L-DMT-L-Lys-L-Phe-NH$_2$ (SBT-140), and D-Arg(butylamidine analog)-L-DMT-L-Lys-L-Phe-NH$_2$ (SBT-149) are useful in the treatment of cardiac ischemia injury (e.g., myocardial infarction) and ischemia-reperfusion injury.

Example 2: Prevention of Cardiac Ischemic Injury and Cardiac Ischemic-Reperfusion Injury This example will show that the peptides of the present technology are useful in the prevention of cardiac ischemic injury and cardiac ischemic-reperfusion injury.
Modified Langendorff Model The Langendorff rodent heart model is widely employed in studies of myocardial function and responses to injury (e.g., ischemia). For whole-heart studies, male Sprague-Dawley rats (7-9 weeks old) are injected with pentobarbital (35 mg/kg, ip injection) and hearts are excised with midline thoracotomy. The aortas are secured around a cannula of a modified Langendorff apparatus and retrogradely perfused (perfusion pressure of 75 mm Hg) with a modified Krebs-Henseleit buffer containing (in mM): 118 NaCl, 24 NaHCO$_3$, 4.75 KCl, 1.2 KH$_2$PO$_4$, 1.2 MgSO$_4$, 2.0 CaCl$_2$, and 10 glucose (gassed with 95/5% O$_2$/CO$_2$). Hearts are bathed in a buffer-filled perfusion chamber maintained at 37° C. for the duration of the experiments. Following the initiation of perfusion, hearts are instrumented for the simultaneous observation of mechanical and electrical function. A buffer-filled latex balloon (size 5, Harvard Apparatus, Holliston, Mass., USA), which is calibrated at the beginning of each day using a digital manometer, is inserted into the left ventricle (via the mitral valve) for the measurement of left ventricular developed pressure (LVDP), with balloon volume adjusted to establish a diastolic pressure of 5-8 mm Hg. Three electrodes are placed into the buffer filled perfusion chamber for the measurement of the volume-conducted electrocardiogram (ECG). Coronary flow rates are monitored constantly with a flow probe (Transconic Systems, Ithaca, N.Y., USA) connected in series with the perfusion line, and normalized to heart wet weight (in grams) at the end of each experiment. All physiological parameters are continuously monitored and stored on a personal computer using commercially available software (Chart, AD Instruments, Colorado Springs, Colo., USA). Heart rate is calculated using the LVDP trace, and maximal rates of contraction (+dP/dt) and relaxation (−dP/dt) are calculated using the derivative of the LVDP trace.
Ischemia/Reperfusion Protocol and Peptide Treatments Prior to the initiation of ischemia/reperfusion, the excised rat hearts are bathed in buffer containing an experimental peptide at a concentration of 1 μM or buffer alone (control) for two hours. The experimental peptide is selected from D-Arg-D-Dmt-D-Lys-L-Phe-NH$_2$ (SBT-46), D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$ (SBT-100), D-Arg-L-DMT-L-Orn-L-Phe-NH$_2$ (SBT-102), D-Orn-L-DMT-L-Lys-L-Phe-NH$_2$(SBT-131), D-(Amidine)Arg(propylamine)-L-DMT-L-Lys-L-Phe-NH$_2$(SBT-140), and D-Arg(butylamidine analog)-L-DMT-L-Lys-L-Phe-NH$_2$ (SBT-149). Following a 10 minute baseline period, ischemia/reperfusion is initiated. Hearts are exposed to global no-flow ischemia by stopping perfusion for 20 min. At the end of the index ischemia, static buffer from the perfusion lines is washed out (via an accessory port proximal to the aortic cannula), and reperfusion ensues for 2 hours with Krebs buffer. At the end of reperfusion, the left ventricle is dissected, sliced into 5 mm-thick slices, incubated in 1% triphenyltetrazolium chloride (TTC) for 10 min (37° C.) and digitally photographed for subsequent infarct size analysis. Infarct size is expressed as a percentage of the left ventricle (% area at risk (AAR))(calculated using ImageJ software, NIH, Bethesda, Md., USA).
Results It is anticipated that treatment with D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$ (SBT-100), D-Orn-L-DMT-L-Lys-L-Phe-NH$_2$(SBT-131), D-(Amidine)Arg(propylamine)-L-DMT-L-Lys-L-Phe-NH$_2$ (SBT-140), or D-Arg(butylamidine analog)-L-DMT-L-Lys-L-Phe-NH$_2$ (SBT-149) will prevent or reduce cardiac ischemia injury and ischemia-reperfusion injury and/or prevent or reduce symptoms of cardiac ischemia injury and ischemia-reperfusion injury as compared to rats treated with D-Arg-D-Dmt-D-Lys-L-Phe-NH$_2$ (SBT-46) or D-Arg-L-DMT-L-Orn-L-Phe-NH$_2$ (SBT-102) and controls. It is anticipated that rats treated with D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$(SBT-131), D-(Amidine)Arg(propylamine)-L-DMT-L-Lys-L-Phe-NH$_2$(SBT-140), or D-Arg(butylamidine analog)-L-DMT-L-Lys-L-Phe-NH$_2$ (SBT-149) will have reduced infarct size, increased LVDP, increased maximal rates of contraction (+dP/dt), and increased maximal rates of relaxation (−dP/dt) as compared to rats treated with D-Arg-D-Dmt-D-Lys-L-Phe-NH$_2$ (SBT-46) or D-Arg-L-DMT-L-Orn-L-Phe-NH$_2$ (SBT-102) and controls.

These results will show that D-Arg-L-DMT-L-Ala-L-Phe-NH$_2$ (SBT-68), (Ac)-D-Arg-L-DMT-L-Lys-L-Phe-NH$_2$ (SBT-85), D-Arg-L-Dmt-L-His-L-Phe-NH$_2$(SBT-100), D-Orn-L-DMT-L-Lys-L-Phe-NH$_2$(SBT-131), D-(Amidine)Arg(propylamine)-L-DMT-L-Lys-L-Phe-NH$_2$(SBT-140), and D-Arg(butylamidine analog)-L-DMT-L-Lys-L-Phe-NH$_2$ (SBT-149) are useful in the prevention of cardiac ischemia injury (e.g., myocardial infarction) and ischemia-reperfusion injury.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A peptide, wherein the peptide is selected from the group consisting of D-Arg-L-DMT-L-Ala-L-Phe-NH$_2$ (SBT-68), D-Arg-L-Dmt-L-His-L-Phe-NH$_2$(SBT-100), D-Orn-L-DMT-L-Lys-L-Phe-NH$_2$ (SBT-131), D-(Amidine)Arg(propylamine)-L-DMT-L-Lys-L-Phe-NH$_2$) (SBT-140), and D-Arg(butylamidine analog)-L-DMT-L-Lys-L-Phe-NH$_2$) (SBT-149), or a pharmaceutically acceptable salt thereof.

2. A composition comprising at least one peptide, wherein the at least one peptide is selected from the group consisting of D-Arg-L-DMT-L-Ala-L-Phe-NH$_2$ (SBT-68), D-Arg-L-Dmt-L-His-L-Phe-NH$_2$(SBT-100), D-Orn-L-DMT-L-Lys-L-Phe-NH) (SBT-131), D-(Amidine)Arg(propylamine)-L-DMT-L-Lys-L-Phe-NH$_2$) (SBT-140), and D-Arg(butylamidine analog)-L-DMT-L-Lys-L-Phe-NH$_2$) (SBT-149), or a pharmaceutically acceptable salt thereof.

3. A method for treating ischemia-reperfusion injury in a subject in need thereof comprising administering to the subject a therapeutically effective amount of a composition comprising at least one peptide of claim 1.

4. A method for treating cardiac ischemia-reperfusion injury in a subject in need thereof comprising administering to the subject a therapeutically effective amount of a composition comprising at least one peptide of claim 1.

5. A method for treating a myocardial infarction in a subject in need thereof comprising administering to the subject a therapeutically effective amount of a composition comprising at least one peptide of claim 1.

6. The method of any one of claims 3-5, wherein the peptide is administered orally, topically, systemically, intravenously, subcutaneously, intraperitoneally, or intramuscularly.

* * * * *

UNITED STATES PATENT AND TRADEMARK OFFICE
CERTIFICATE OF CORRECTION

PATENT NO. : 11,548,913 B2  
APPLICATION NO. : 16/067514  
DATED : January 10, 2023  
INVENTOR(S) : Scott Duncan Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 257 days.

Signed and Sealed this  
Thirty-first Day of December, 2024

Derrick Brent  
*Acting Director of the United States Patent and Trademark Office*